(12) United States Patent
Shashidhar

(10) Patent No.: US 8,415,624 B2
(45) Date of Patent: Apr. 9, 2013

(54) DIFFERENTIAL WAVELENGTH IMAGING METHOD AND SYSTEM FOR DETECTION AND IDENTIFICATION OF CONCEALED MATERIALS

(75) Inventor: Ranganathan Shashidhar, Needham Heights, MA (US)

(73) Assignee: Polestar Technologies, Inc., Needham Heights, MA (US)

(*) Notice: Subject to any disclaimer, the term of this patent is extended or adjusted under 35 U.S.C. 154(b) by 642 days.

(21) Appl. No.: 12/660,348

(22) Filed: Feb. 25, 2010

(65) Prior Publication Data
US 2010/0278441 A1  Nov. 4, 2010

Related U.S. Application Data

(63) Continuation-in-part of application No. 11/544,368, filed on Oct. 6, 2006, now abandoned.

(60) Provisional application No. 60/724,321, filed on Oct. 6, 2005.

(51) Int. Cl.
*G01R 23/02* (2006.01)

(52) U.S. Cl.
USPC .............. 250/339.11; 250/339.14; 250/341.8; 250/342

(58) Field of Classification Search .................. 250/339; 382/191, 203
See application file for complete search history.

(56) References Cited

U.S. PATENT DOCUMENTS

| | | | |
|---|---|---|---|
| 4,853,543 A * | 8/1989 | Ozdemir | 250/372 |
| 6,373,558 B1 * | 4/2002 | Hasson | 356/4.07 |
| 7,010,455 B2 | 3/2006 | Pieragostini et al. | |
| 7,239,974 B2 | 7/2007 | Gulati | |
| 7,417,727 B2 | 8/2008 | Polonskiy et al. | |
| 7,599,732 B2 | 10/2009 | Sevick-Muraca et al. | |
| 7,623,233 B2 | 11/2009 | Freese et al. | |
| 2005/0010374 A1 * | 1/2005 | Li | 702/28 |
| 2006/0157652 A1 | 7/2006 | Treado et al. | |
| 2007/0118324 A1 | 5/2007 | Gulati | |
| 2008/0191137 A1 | 8/2008 | Poteet et al. | |
| 2008/0195347 A1 | 8/2008 | Gatt | |
| 2009/0107758 A1 | 4/2009 | Moore | |
| 2009/0236528 A1 | 9/2009 | Shpantzer et al. | |

OTHER PUBLICATIONS

Bernadette Johnson et al., a compact active hyperspectral imaging system for the detection of concealed targets, pp. 144-153, Apr. 1999, SPIE.*

* cited by examiner

*Primary Examiner* — David Porta
*Assistant Examiner* — Taeho Jo
(74) *Attorney, Agent, or Firm* — Burns & Levinson LLP; Orlando Lopez

(57) ABSTRACT

A method and system for detection and identification of concealed materials, is provided, wherein a dark image and two or more NIR sample images are taken at two or more key wavelengths or bands of wavelengths corresponding to peaks and/or valleys in the NIR spectra of known materials, and differential wavelength imaging processes are used to produce a differential wavelength image based on therein. The differential wavelength image is then analyzed/processed so as to detect any materials concealed on the target of interest, such as a human or piece of baggage, by calculation of pixel intensity values in the image and identification of distinctive pixel values. Then, via various methods, the distinctive pixel values of the detected materials are compared to a data set of known wavelengths related to known materials, such as explosives and other contraband. Correspondence thereof results in an accurate identification of the concealed material(s).

29 Claims, 29 Drawing Sheets
(20 of 29 Drawing Sheet(s) Filed in Color)

DIFFERENTIAL WAVELENGTH IMAGING METHOD AND SYSTEM FOR DETECTION AND IDENTIFICATION OF CONCEALED MATERIALS

CROSS REFERENCE TO RELATED APPLICATIONS

The present application claims priority of non-provisional application Ser. No. 11/544,368, filed Oct. 6, 2006, and provisional application Ser. No. 60/724,321, filed Oct. 6, 2005, now abandoned, the entire contents of both of which are hereby incorporated herein by reference.

STATEMENT REGARDING FEDERALLY SPONSORED RESEARCH OR DEVELOPMENT

This invention was made with Government support under contact #W31P4Q-09-C-0585 awarded by U.S. Army Contract Command. The Government has certain rights in the invention.

BACKGROUND OF THE INVENTION

1. Field of the Invention

The present invention provides a differential wavelength imaging method for chemical analysis and infrared imaging, and more particularly, to detect concealed explosives, drugs, or other contraband materials, hidden under clothing, at security checkpoints at airports, border crossings, government buildings, and military facilities, and identify same. Specifically, the present invention provides a method of differential wavelength imaging capable of standoff detection and identification of contraband materials when they are concealed on a person under clothing, in a backpack, or concealed in bags not worn on a person, and identify same using NIR wavelength differential imaging techniques, and system for carrying out same.

2. Description of the Related Art

Numerous conventional approaches have been taken in the field of standoff detection and identification to attempt to detect and identify materials, especially explosives, drugs, etc., concealed under clothing. Such conventional approaches that have been reported in the literature for standoff detection and identification of concealed contraband materials include: x-ray backscatter imaging, neutron excited gamma ray emission spectroscopy, terahertz reflection spectroscopy, and laser induced breakdown spectroscopy.

Literature references concerning these approaches include: National Research Council of the National Academies, "Existing and Potential Standoff Explosives Detection Techniques," National Academies Press, Washington D.C., (2004); C. Bruschini, "Commercial Systems for the Direct Detection of Explosives (for Explosive Ordnance Disposal Tasks," ExploStudy, Final Report, Swiss Defense Procurement Agency, http://diwww.epfl.ch/lami/detec/explostudy.html, (2001); "Terahertz waves penetrate the world of imaging," Opto & Laser Europe, October (2002), http://optics.org/articles/ole/7/9/5/1; Martens and T. Naes, *Multivariate Calibration*, J. Wiley & Sons, New York (1989); H. Seisler, Y. Ozaki, S. Kawata, and H. Heise, Near-Infrared Spectroscopy—Principles, Instruments, Applications, chapter 7 "Chemometrics in Near-Infrared Spectroscopy," Wiley-VCH, (2002); H. Mark, et. al., Analytical Chemistry, 57, 1449 (1985); C. Lopez-Moreno, S. Palanco, J. Javier Laserna, F. DeLucia Jr, A. W. Miziolek, J. Rose, R. A. Walters and A. I. Whitehouse, "Test of a stand-off laser-induced breakdown spectroscopy sensor for the detection of explosive residues on solid surfaces," J. Analytical Atomic Spectrometry, 21, 55-60 (2006).

Problems with the x-ray backscattering imaging approach include: poor chemical selectivity for chemical identification with high potential for false positives, large size and weight of instrumentation which prevents the system from being man-portable, and human health risk from x-ray exposure.

Problems with neutron excited gamma ray spectroscopy include: limited chemical selectivity resulting from the measurement only producing elemental concentration results, limited sensitivity, and long measurement times at significant standoff distances (i.e. 1 ft. or greater), and substantial human health risks. Measurements providing only elemental analysis information would not be likely to be able to identify explosive materials such as triacetaone-triperoxide that contain only the elements C, H, and O, and identification of drugs would be very difficult.

Problems with terahertz spectroscopy include: slow measurement time, as well as substantial problems with interference from absorption of terahertz radiation by atmospheric water vapor for standoff distances greater than 10 ft. In addition, the size and weight of the equipment are too great for man-portability.

Laser induced breakdown spectroscopy (LIBS) is a trace detection method that can detect and identify small particles of explosive or other materials on the outside of a surface in a standoff mode. The primary problem with LIBS is that it cannot detect or identify materials concealed underneath a covering layer such as cloth and can only detect explosive particles on the outside surface of clothing. Explosives or other contraband materials that are well sealed in a plastic bag and concealed under clothing, where the outside surface of the clothing was not contaminated with the dust of the contraband material, could not be detected or identified with LIBS.

Further, NIR spectroscopy has been used to identify chemical compounds. In particular, Li, et al., in U.S. Patent Publication No. 2005/0010374, discloses a method of analyzing NIR data, so as to identify various solid forms of chemical compounds and drug candidates. This method includes the steps of: (1) computing the second derivative spectra for collected NIR spectra; (2) applying principal component analysis (PCA) of the second derivative spectra at predetermined wavelengths either the entire wavelength region or a selected wavelength region for segregating the samples; identifying the groups and group membership from the PCA graph, and further evaluating group members by calculating Mahalanobis distances of a given group to assess qualification of the group members. However, this method is merely an initial exploratory analysis of near-infrared spectra designed to identify how many different components or materials are present in an unknown sample, and how different their spectra are.

Additional conventional methods include using NIR spectroscopy to attempt to identify components relative to a saved calibration library, via identification of absorption wavelengths, and comparison thereof to known standards. For example, U.S. Pat. No. 7,239,974, to Gulati, discloses an explosive device detection method and system based on differential emissivity. This method and system monitors the emissivity levels of target subjects in monitored zones by repeatedly scanning the pixels of an infrared photodetector array, and then processing the pixel values to determine if they correspond to at least one calibrated emissivity level associated with a concealed explosive device. The calibration techniques of Gulati involve attempts to eliminate the effects of clothing and other personal items, as well as environmental factors, but suffer from a concentration mainly on differences in emissivity levels caused by distance of the target from the source (IR photodetector), rather than increasing the contrast/difference in measured emissivity between the covering materials and the concealed contraband materials.

Further, such conventional methods are inaccurate, when used to attempt to identify materials concealed under clothing, covering materials, etc., due to the difficulties inherent in filtering out the wavelengths reflected from the clothing, covering materials, containment materials, etc., as well as, importantly, ambient light, sunlight, etc. Thus, to obtain accurate measurements, such conventional NIR methods generally are confined to laboratory or laboratory-like environments, not public areas, such as airports.

In view of the above, it is an object of the present invention to overcome the disadvantages of the prior art, as described above, and provide a method to efficiently and accurately detect and identify concealed materials, such as explosives, drugs, or hazardous materials, concealed on a person under clothing or in a backpack, or concealed in unattended paper, plastic, cloth or leather bags (including backpacks), and a system for carrying out same. The detection method of the present invention is preferably performed at some finite distance from the material being detected, which is referred to as the "standoff distance". The standoff distance could be in the range of from 1 cm to 100 m. In all cases, the material being detected may be concealed under some type of covering materials such as cloth, paper, plastic, or leather that has substantial optical absorption and/or light scattering properties which obscures viewing the concealed material under the covering material with light in the visible wavelength range (400-700 nm).

It is a further object of the present invention to provide such a system and method as described above, wherein the system and method may identify the concealed material without the use of reference images (such as dark images).

BRIEF SUMMARY OF THE INVENTION

In order to achieve the objects of the present invention as described above, the present inventors earnestly endeavored to develop a method capable of detecting and identifying materials concealed by one or more covering materials at various standoff distances. As a result of these endeavors, the present inventors have developed a differential wavelength imaging method for detecting and identifying of materials of interest concealed by one or more covering materials. The covering materials may be any materials which block or decrease the visibility of the material(s) of interest, but which do not completely block or reflect light. In particular, the method of the present invention is applicable to covering materials such as cotton, cotton/polyester blends, silk, polypropylene, nylon, nylon/cotton blends, rayon, wool, flannel, leather, and combinations thereof, and concealed materials such as explosives and contraband items.

The differential wavelength imaging method of the present invention involves producing a differential wavelength image by capturing a plurality of sample images of a target, compiling a plurality of processed image pixel values associated with the sample images, evaluating the total processed image data so as to detect any concealed materials by identifying pixels having a higher or lower intensity value than the covering materials, and identifying any known concealed materials by comparing each processed image pixel value with the NIR reflection spectra of known contraband materials to determine correspondence therewith.

The differential wavelength imaging system of the present invention, designed to implement the method described above, is generally comprised of a number of hardware elements including a computer, a computer memory storage device in communication with the computer, NIR signal processing electronics integral with or in communication with the computer, a near-infrared (NIR) range camera in communication with the NIR signal processing electronics, and an optical filtering means disposed adjacent to or integral with the NIR range camera, said optical filtering means operable to filter light at two or more selected wavelengths. The computer may be any conventional general use computer processor, and the computer memory storage device may be any conventional computer memory device.

In addition, the present system preferably employs a spectral collection and chemical identification application program code, executed on the computer or on a computer in communication therewith, which is operable to identify the materials of interest concealed by the covering materials via NIR differential wavelength imaging. In particular, the spectral collection and chemical identification application carries out the method described above in a computer implemented manner. In a further preferred embodiment, the differential wavelength imaging system of the present invention described above further comprises a light source disposed in proximity to the materials of interest, so as to be operable to reflect light thereon. The light source may be any conventional light source, and may even include sunlight.

Additional aspects of the invention will be set forth in part in the description which follows, and in part will be obvious from the description, or may be learned by practice of the invention. The aspects of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE SEVERAL VIEWS OF THE DRAWING

The patent or application file contains at least one drawing/photograph executed in color. Copies of this patent or patent application publication with color drawing(s)/photographs will be provided by the Office upon request and payment of the necessary fee. The accompanying drawings, which are incorporated in and constitute part of this specification, illustrate embodiments of the invention and together with the description, serve to explain the principles of the invention. The embodiments illustrated herein are presently preferred, it being understood, however, that the invention is not limited to the precise arrangements and instrumentalities shown, wherein.

DETAILED DESCRIPTION OF THE INVENTION

Figure 1:
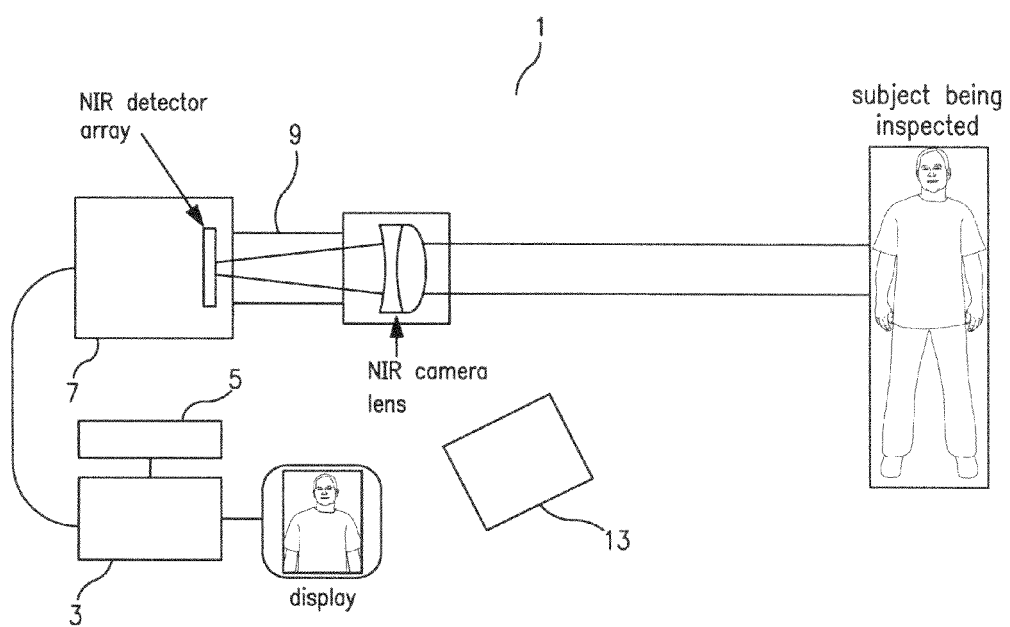
FIG. 1 is a block diagram illustrating the components and the connectivity thereof which make up the differential wavelength imaging system for detection and identification of concealed materials, in which a variable wavelength filter system is provided.

There is a substantial attenuation of light in the NIR spectral range by cloth, which is normally on the order of 10,000 or more for NIR light that passes through two or more layers of cloth, reflects off of concealed materials, and then passes back through the cloth/concealing layers a second time. After passing through the cloth/concealing layers the second time, according to the method of the present invention, the reflected NIR light is received by the NIR camera of the present system. However, because of this large attenuation factor by the cloth/concealing layers, imaging at a single wavelength in the NIR spectral range does not show the presence of the concealed materials or objects concealed under the covering cloth, a major difficulty experienced with conventional detections systems and methods as described above.

However, the present inventors unexpectedly discovered that interfering contributions by the covering/concealing layers and variations in NIR illumination intensity can be largely eliminated by utilizing a differential wavelength imaging method as described herein, resulting in selective imaging of materials concealed under the covering/concealing layers. Furthermore, it was discovered that by using the method described herein, no reference image was need, thereby providing a much faster imaging process, and allowing the method and system to be utilized in busy locations, such as airports, major event locations, etc.

Accordingly, the present invention provides a differential wavelength imaging method for detection and identification of concealed materials, and system for carrying out same. In particular, the method and system of the present invention are capable of detecting and identifying chemicals, explosives, contraband of interest, etc. concealed under such covering materials as cotton, cotton/polyester blends, silk, polypropylene, nylon, nylon/cotton blends, rayon, wool, flannel, leather, and combinations thereof.

As mentioned above, the differential wavelength imaging method of the present invention involves producing a differential wavelength image by capturing a plurality of sample images of a target, such as a person. These sample images are captured by, for example, an NIR camera. Each image is comprised of a plurality of pixels, and each pixel has a pixel value based on intensity. A plurality of processed image pixel values associated with the sample images are then compiled to produce total processed image data, and the total processed image data is then evaluated so as to identify pixels having a higher or lower intensity value than the covering materials. Thereafter, the processed image pixel values of the pixels having a higher or lower intensity value than the covering materials are compared with the NIR reflection spectra of known contraband materials to determine correspondence therewith.

In a preferred embodiment, the differential wavelength imaging method of the present invention begins with selecting one or more NIR reflection spectra of known materials, both covered by a concealing material such as cloth, etc., and uncovered. Then, two or more key NIR wavelengths are selected for each NIR reflection spectra of the known material. Preferably, these key NIR wavelengths are chosen at distinctive peaks and/or valley in the NIR spectra of the known materials.

Figure 4:
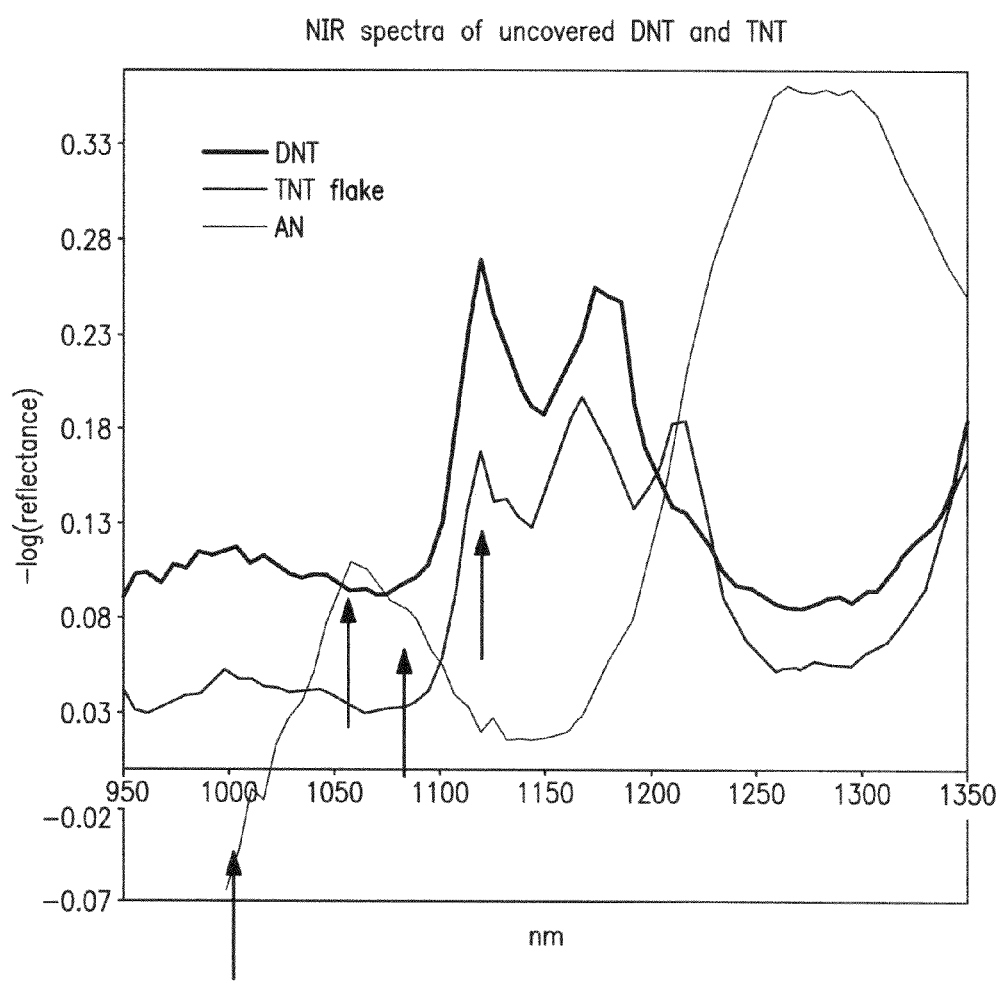
FIG. 4 is a NIR reflection spectra showing the reflectance spectrum of uncovered trinitrotoluene (TNT), dinitrotoluene (DNT) and ammonium nitrate (AN) taken from single pixels of hyperspectral image data, in which the wavelengths that are desirable for use in selective differential wavelength imaging are denoted by the arrows.
Figure 5:
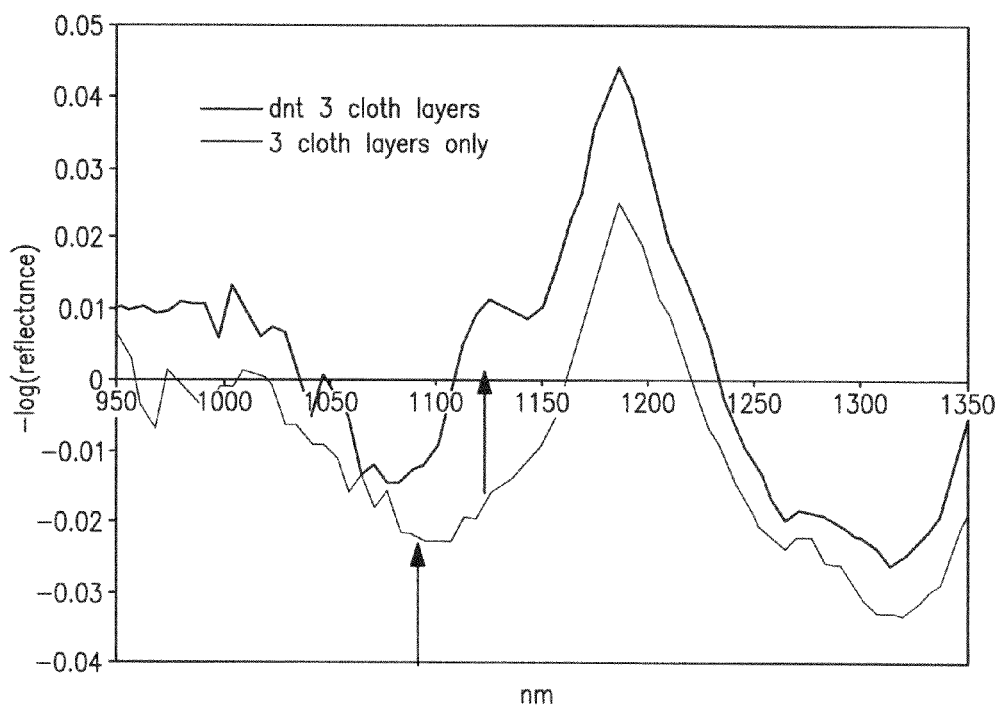
FIG. 5 is a NIR reflection spectra showing the reflectance spectrum of dinitrotoluene (DNT) under 3 cloth layers, as well as the spectrum of the same 3 cloth layers alone, taken from single pixels of hyperspectral image data, in which the wavelengths that are desirable for use in selective differential wavelength imaging of DNT are denoted by the arrows.

Specifically, as illustrated by the arrows inserted into the spectra shown in FIGS. 4 and 5, two or more key NIR wavelengths (corresponding to distinguishing wavelengths) are selected for each NIR reflection spectra of the known material. NIR imaging is then carried out at such specific pairs of wavelength bands wherein each pair of wavelengths corresponds to adjacent peaks and valleys in the NIR reflectance spectra of a specific known material (such as an explosive compound).

Figure 6:
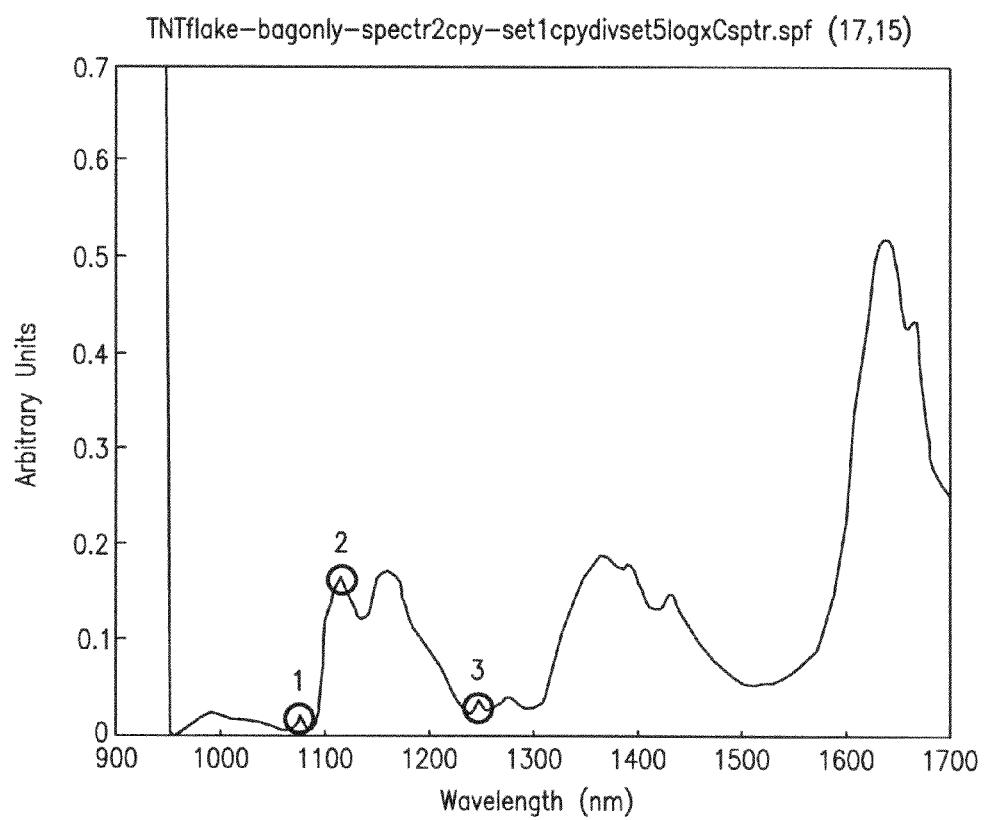
FIG. 6 is a NIR reflection spectra showing the reflectance spectrum of trinitrotoluene (TNT) in flake form contained in a polyethylene antistatic bag held in a polyethylene vest pocket, taken from single pixels of hyperspectral image data, in which the wavelengths that are desirable for use in generating a 3 wavelength (2 off-peak and 1 peak) differential wavelength image.

For example, as illustrated in FIGS. 4 and 5, these NIR reflection spectra for known materials include NIR spectra of the known material collected with no covering material, and, as illustrated in FIG. 5, one or more NIR spectra of the known material collected with one or more layers of known covering materials covering same. To further increase the visibility of the concealed material and provide increased chemical selectivity relative to other known materials, additional key NIR wavelengths of known materials may be collected for later reference. For example, as illustrated in FIG. 6, three identified key wavelengths (identified by the circles and numbers 1, 2, 3 inserted in the NIR spectra) are shown for TNT in flake form contained in a polyethylene antistatic bag held in a polyethylene vest pocket. These 3 key wavelengths, representing 2 off-peak points in the spectra and 1 peak, may then be used in generating a 3 wavelength differential wavelength image.

After the selection processes above are carried out, one or more dark images are collected. These dark images are collected, for example, via mechanically covering the NIR camera lens so as to prevent all light from entering the camera. Alternatively, an electronic means of collection may be used, or a combination of electronic and mechanical means, may be used to collect the dark image. The collected dark image data is collected, and an image pixel value is measured for each measured pixel, so as to determine a base (dark) image pixel value.

Figure 8:
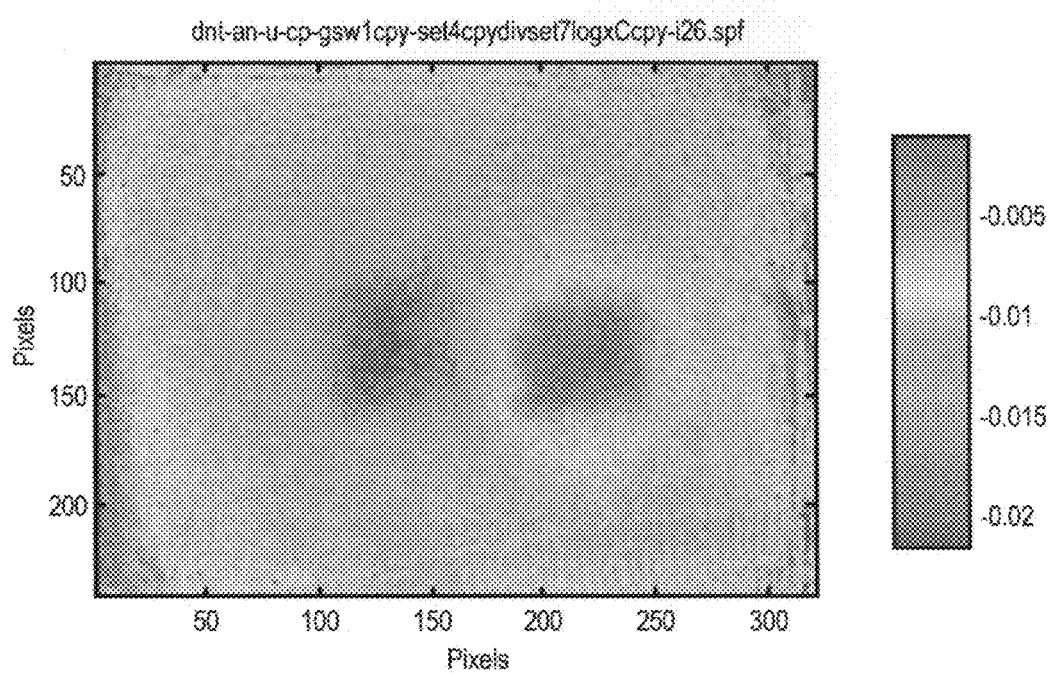
FIG. 8 is a color NIR differential wavelength image of two 2"×2" bags of DNT and AN concealed under 3 cloth layers, measured between 1190 and 1051.5 nm.
Figure 9:
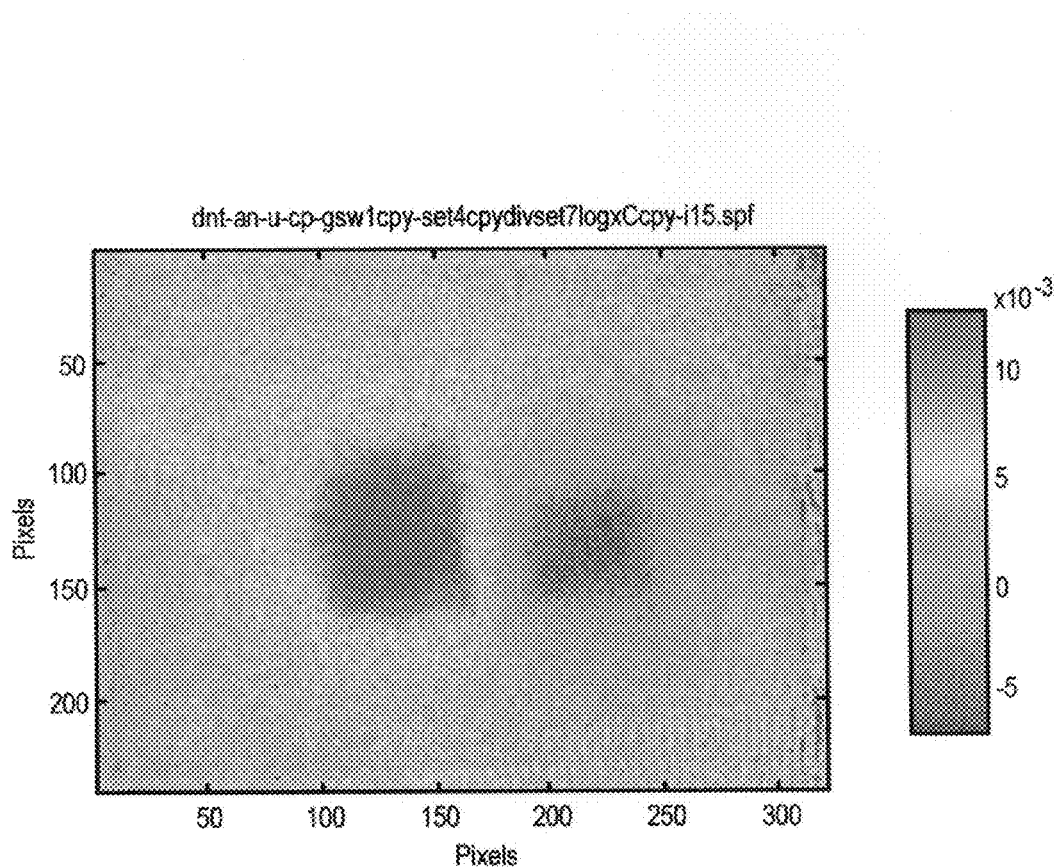
FIG. 9 is a color. NIR differential wavelength image of the two 2"×2" bags of DNT and AN concealed under 3 cloth layers shown in FIG. 8, however measured between 1133.3 and 1084.8 nm.
Figure 10:
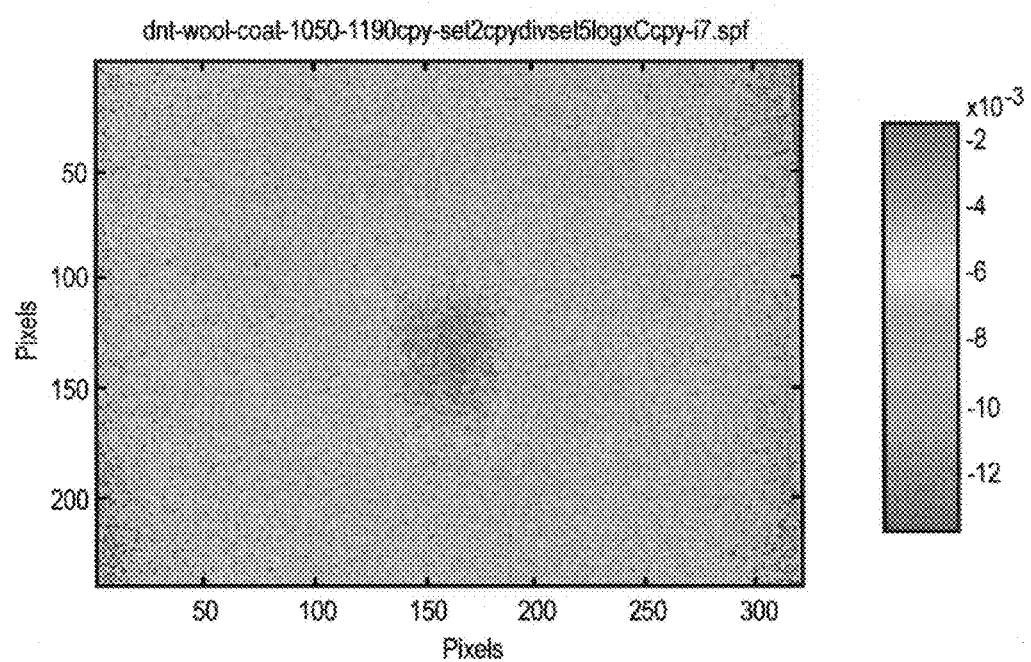
FIG. 10 is a color NIR differential wavelength image of a 20 g bag of DNT concealed under an approximately 5 mm thick heavy dark blue colored wool winter coat, measured between 1117.0 and 1086.5 nm.
Figure 13:
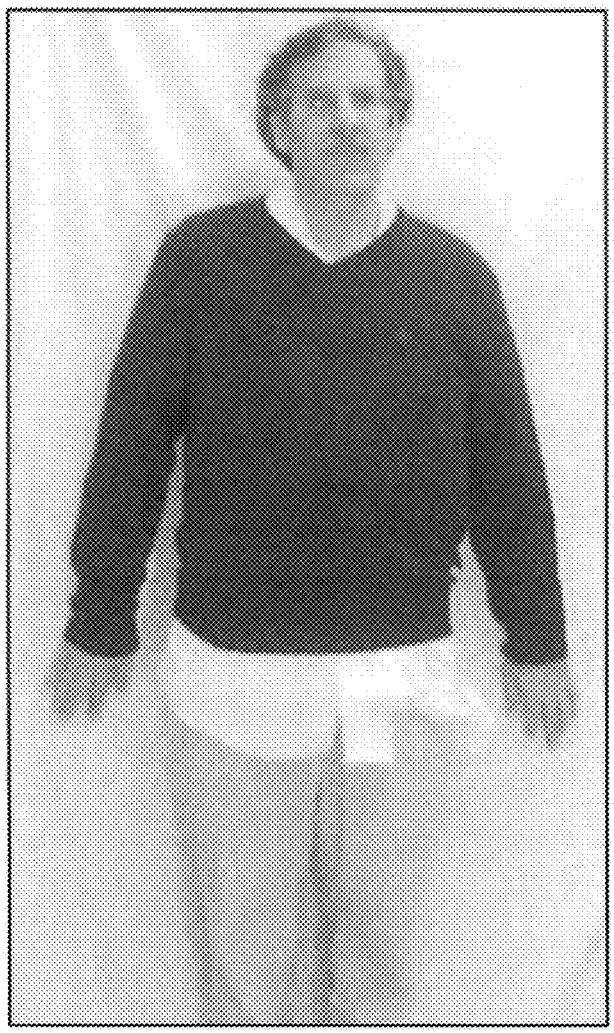
FIG. 13 is a color visible wavelength photograph of the human subject shown in FIG. 12, having 3 additional cloth layers (undershirt, dress shirt and wool sweater) covering the polyethylene vest containing the bags of DNT.
Figure 14:
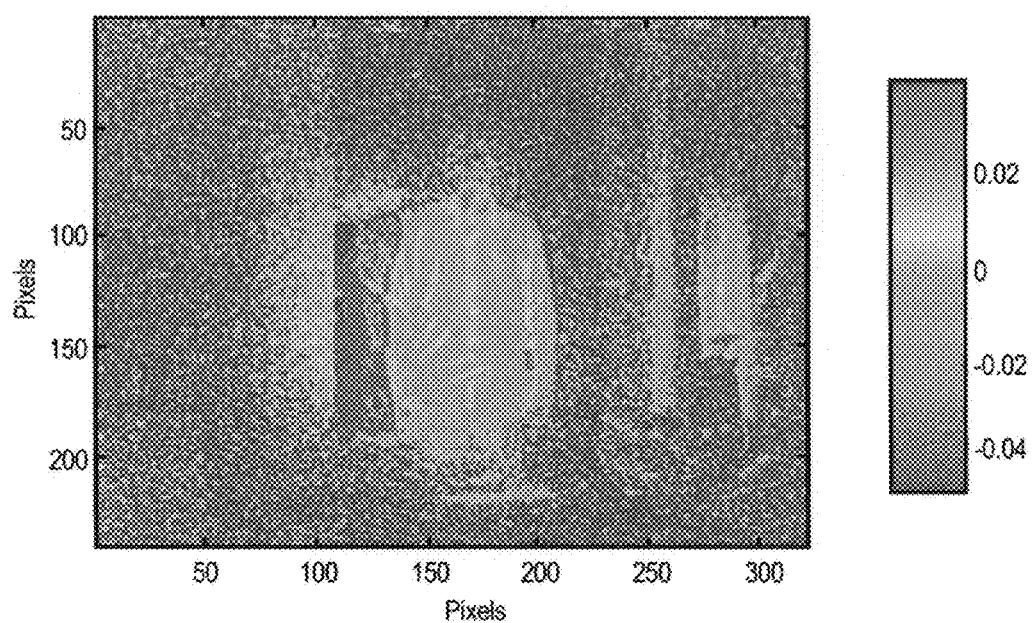
FIG. 14 is a color NIR differential wavelength image, taken at a standoff distance of 25 feet using the experimental setup shown in FIG. 11 of the human subject shown in FIG. 13 wearing a polyethylene vest (without bags of DNT contained therein) under 3 outer cloth layers.
Figure 15:
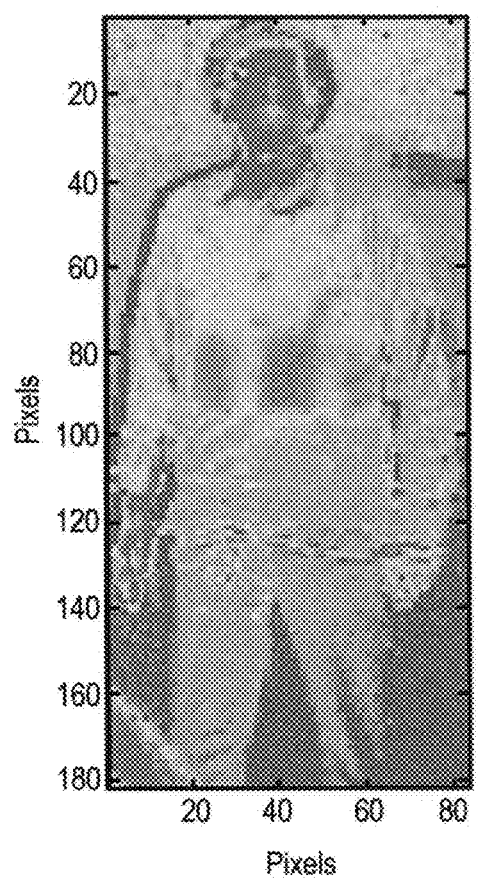
FIG. 15 is a color NIR differential wavelength image, taken at a standoff distance of 25 feet using the experimental setup shown in FIG. 11 of the human subject wearing a polyethylene vest under 3 outer cloth layers shown in FIG. 13.
Figure 16:
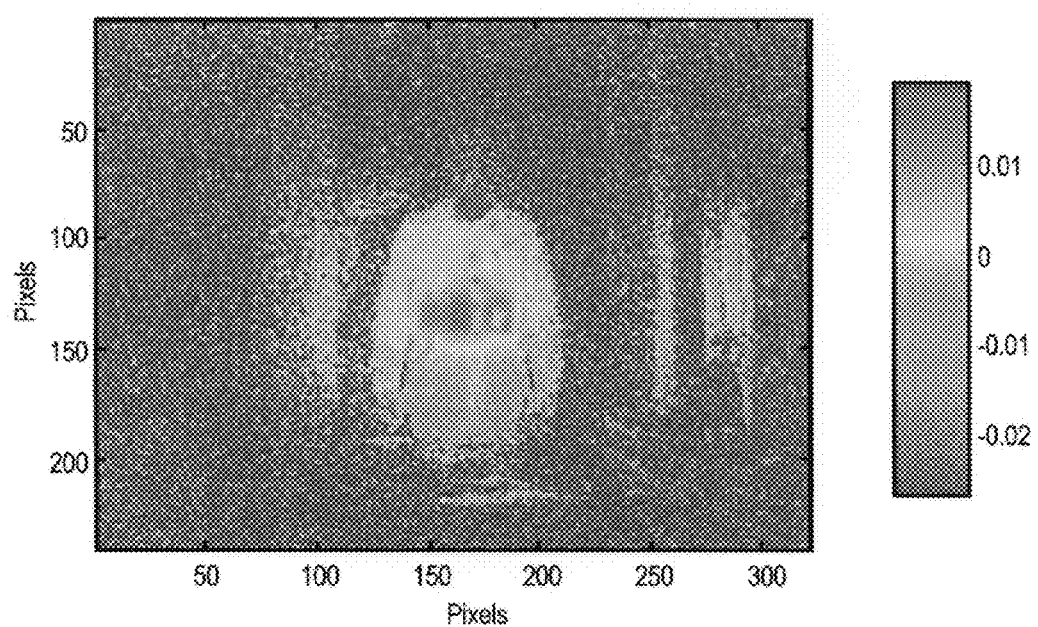
FIG. 16 is a color NIR differential wavelength image, measured with a reference image, of the human subject shown in FIG. 12 taken at a standoff distance of 25 feet using the experimental setup shown in FIG. 13 with a different light source (1000 W tungsten halogen lamp)

Next, as illustrated in FIGS. 8-10, two or more sample images of the sample (i.e., target of interest, such as a person as shown in FIG. 13 possibly having a material concealed beneath their clothing) are collected at each of two or more selected wavelengths or bands of wavelengths. Each sample image is analyzed by determining an image pixel value for each measured pixel in the sample image. Then, a processed image pixel value is calculated for each image pixel. This processed image pixel value is based on the dark image pixel value mentioned above, and each of the sample image pixel values for each of the two or more sample images.

Thereafter, as illustrated in FIGS. 14-17, a differential wavelength image is developed by compiling a plurality of the processed image pixel values from each sample image into one image. In a preferred embodiment, the differential wavelength image is determined with the numerator of the ratio as the wavelength corresponding to an absorption peak of the material of interest, and the denominator corresponding to an absorption valley for ratio processed image data. As shown in FIGS. 14-17, the concealed materials, i.e., both the polyethylene vest and the DNT, are clearly visible in the differential wavelength image.

Figure 18:
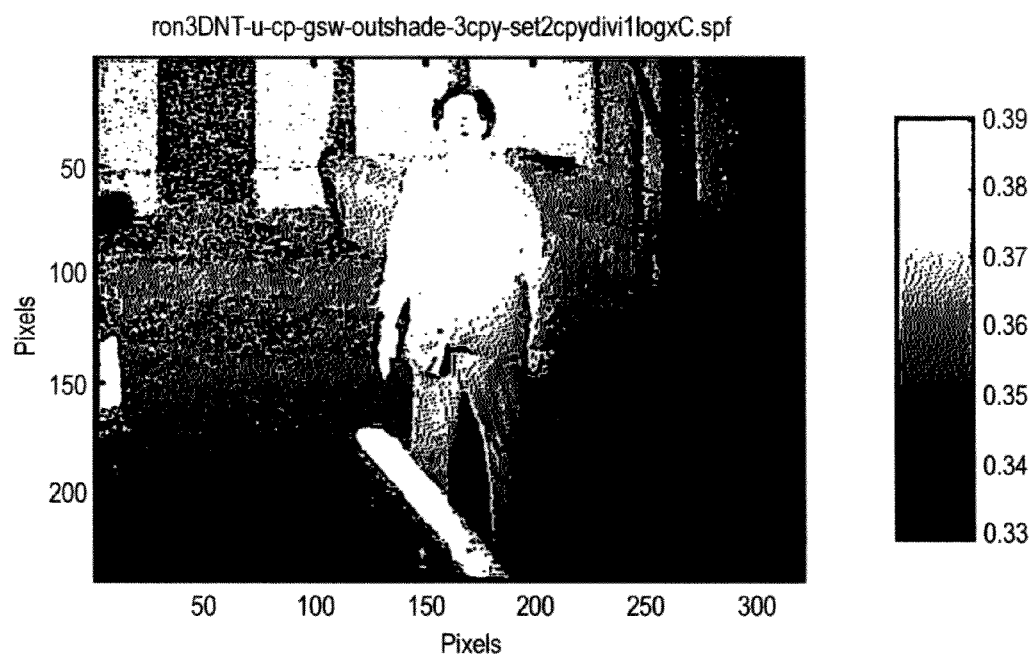
FIG. 18 is a greytone NIR differential wavelength image of a human subject taken under the same conditions as in FIG. 17, in which contrast enhancement has been employed.
Figure 19:
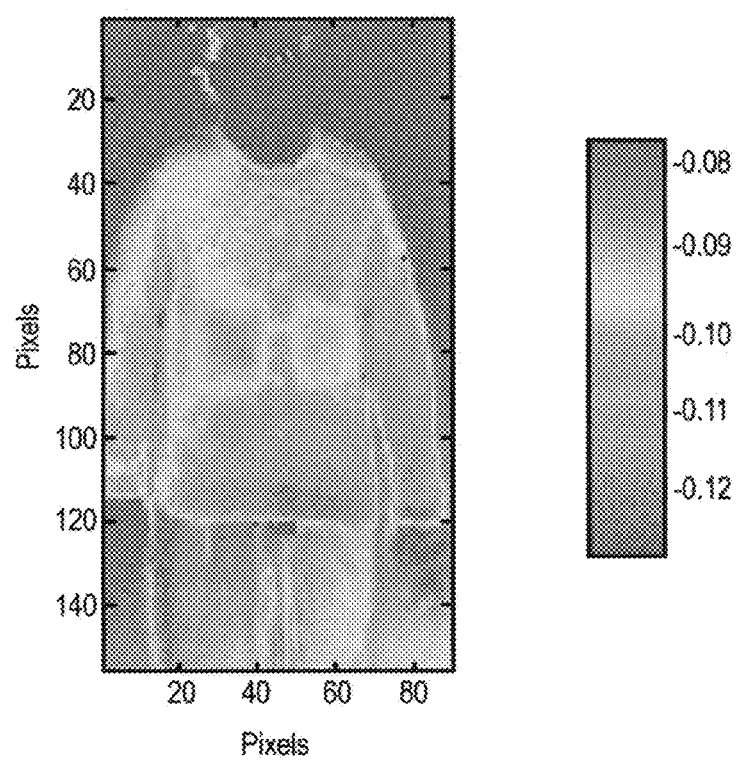
FIG. 19 is a cropped color NIR differential wavelength image, processed with color enhancement, taken at 1117-1086 nm (selective for DNT) of a human subject wearing a polyethylene vest containing 2 one pound bags of DNT concealed under 3 cloth layers, the image taken with the differential wavelength imaging system for detection and identification of concealed materials of the present invention, utilizing a 1000 W tungsten halogen lamp at a standoff distance of about 8 ft. from the subject, and an NIR hyperspectral imaging camera at a standoff distance of about 25 ft. from the subject.
Figure 20:
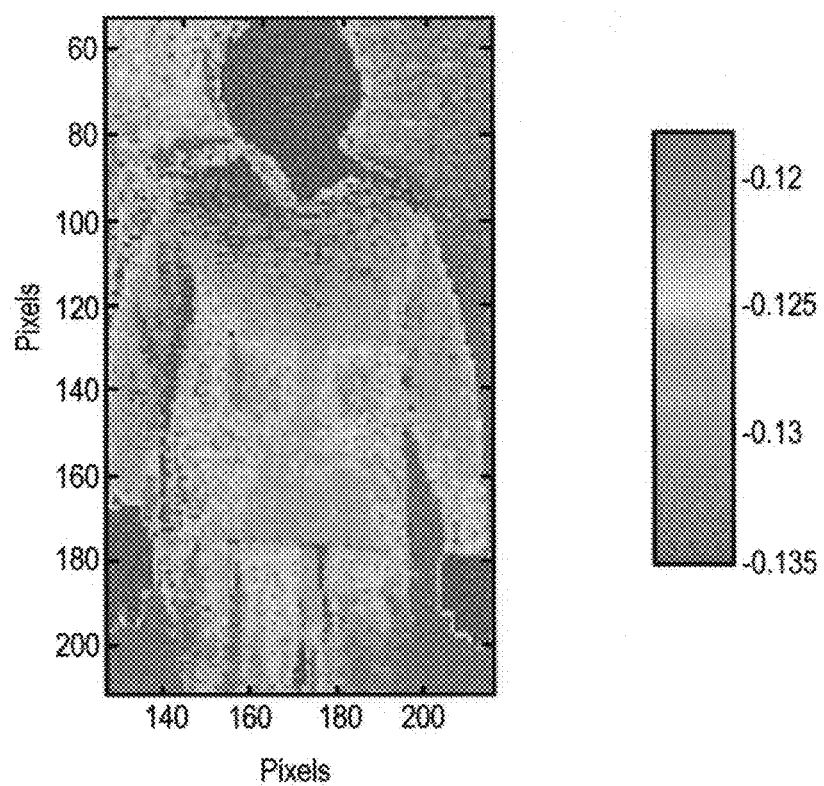
FIG. 20 is a color NIR differential wavelength image taken at 1050-1000 nm (selective for AN) of a human subject wearing a polyethylene vest containing 2 one pound bags of AN concealed under 3 cloth layers, the image taken with the differential wavelength imaging system for detection and identification of concealed materials of the present invention described in FIG. 20.
Figure 21:
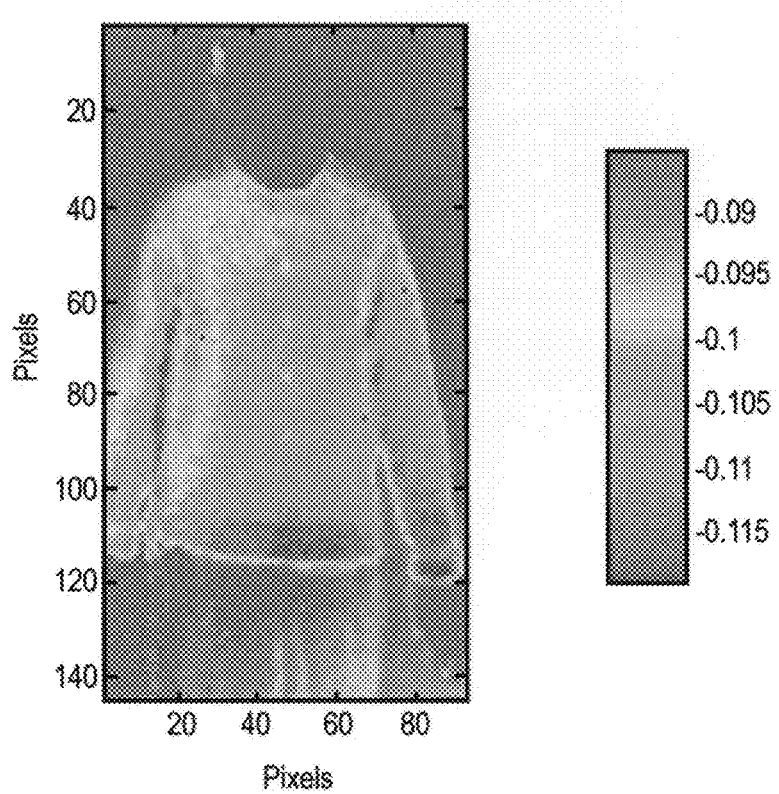
FIG. 21 is a color NIR differential wavelength image taken at 1117-1086 nm (selective for DNT) of a human subject wearing a polyethylene vest containing 2 one pound bags of AN concealed under 3 cloth layers, the image taken with the differential wavelength imaging system for detection and identification of concealed materials of the present invention described in FIGS. 20 and 21, and illustrating the absence of imaging of DNT in the photo.

To further improve the distinction/visibility of the concealed materials (materials of interest) from the covering materials, various preferable techniques may be utilized depending upon the camera/system configuration used. Such enhancement processes may include one or more of pixel histogram normalization, linear or non-linear pixel intensity transformation, and transformation of the image into a binary image using a threshold pixel intensity value for separation of 0 and 1 pixels. For example, as shown in FIG. 18, if a greytone camera is used, contrast enhancement may be applied to the differential wavelength image to increase contrast of the concealed materials. Further, as shown in FIG. 19, when using a color NIR camera, a color enhancement process may be applied to the differential wavelength image to enhance the hues of the colors, thereby increasing the distinguishing character of the concealed materials from the covering materials.

After producing the differential wavelength image, and preferably processing the image to further increase the distinctiveness of the concealed materials, the differential wavelength image (i.e., the total processed image data) is evaluated. This evaluation process consists of recognizing/detecting any concealed materials in the image by first identifying pixels within the differential wavelength image having a higher or lower intensity value than the known covering materials. If and when such pixels having a higher or lower intensity are identified, these pixel intensity values of the processed differential wavelength image are compared to image pixel values of NIR reflection spectra of known materials to determine correspondence therewith.

In a preferred embodiment, the evaluation process involves determining a processed image pixel value for one or more of the pixels in the differential wavelength by calculating a ratioed intensity value (in intensity units) of the two or more differential wavelength images using the following formula A:

$$I_{x,y} = [(Isample^{\lambda 1}{}_{x,y} - Idark^{\lambda 1}{}_{x,y})] / [(Isample^{\lambda 2}{}_{x,y} - Idark^{\lambda 2}x,y)] \quad (A)$$

where $I_{x,y}$ is the processed image pixel value at pixel (x,y), $Isample^{\lambda 1}{}_{x,y}$ is the sample image pixel value at wavelength $\lambda 1$ and pixel (x,y), $Idark^{\lambda 1}{}_{x,y}$ is the dark image pixel value at wavelength $\lambda 1$ and pixel (x,y), $Isample^{\lambda 2}{}_{x,y}$ is the sample image pixel value at wavelength $\lambda 2$ and pixel (x,y), and $Idark^{\lambda 2}x,y$ is the dark image pixel value at wavelength $\lambda 2$ and pixel (x,y).

In an alternative preferred embodiment, the processed image pixel value for one or more of the pixels in the two or more images is determined by calculating a logarithmic value of the ratioed intensity, using the following formula B:

$$\log I_{x,y} = \log [(Isample^{\lambda 1}{}_{x,y} - Idark^{\lambda 1}{}_{x,y}) / (Isample^{\lambda 2}{}_{x,y} - Idark^{\lambda 2}x,y)] \quad (B).$$

Then, any known concealed material is identified by comparing each processed image pixel value with the NIR reflection spectra of known materials to determine correspondence therewith. If there is correspondence of the pixel intensity values of detected concealed materials, the known concealed material is identified to the user via the production of a user report. The user report, for example, comprises data concerning one or more of the detected known materials, an identification of the covering materials, and identification of any other materials of interest shown in the image that correspond to known materials in the database accessed by the computer. The user report may be provided to the user via any known conventional means, such as electronically via an electronic graphical interface, paper printout, audio communication, etc.

As mentioned above, the differential wavelength image may be developed by processing two sample images, i.e., two sets of pixel image values. However, to provide a further improved image in which the visibility of the concealed material is further improved, in a preferred embodiment, three sample images are taken at three selected wavelengths or bands of wavelengths, wherein the processed image value for each pixel is calculated using the following formula (C):

$$I_{x,y} = [[[(Isample^{\lambda 1}{}_{x,y} - Idark^{\lambda 1}{}_{x,y})]/[(Isample^{\lambda 2}{}_{x,y} - Idark^{\lambda 2}x,y)]] + [[(Isample^{\lambda 2}{}_{x,y} - Idark^{\lambda 2}{}_{x,y})]/[(Isample^{\lambda 3}{}_{x,y} - Idark^{\lambda 3}x,y)]]]/2 \quad (C)$$

where $I_{x,y}$ is the processed image pixel value at pixel (x,y), $Isample^{\lambda 1}{}_{x,y}$ is the sample image pixel value at wavelength $\lambda 1$ and pixel (x,y), $Idark^{\lambda 1}{}_{x,y}$ is the dark image pixel value at wavelength $\lambda 1$ and pixel (x,y), $Isample^{\lambda 2}{}_{x,y}$ is the sample image pixel value at wavelength $\lambda 2$ and pixel (x,y), $Idark^{\lambda 2}x,y$ is the dark image pixel value at wavelength $\lambda 2$ and pixel (x,y), $Isample^{\lambda 3}{}_{x,y}$ is the sample image pixel value at wavelength $\lambda 3$ and pixel (x,y), and $Idark^{\lambda 3}x,y$ is the dark image pixel value at wavelength $\lambda 3$ and pixel (x,y).

Figure 7:
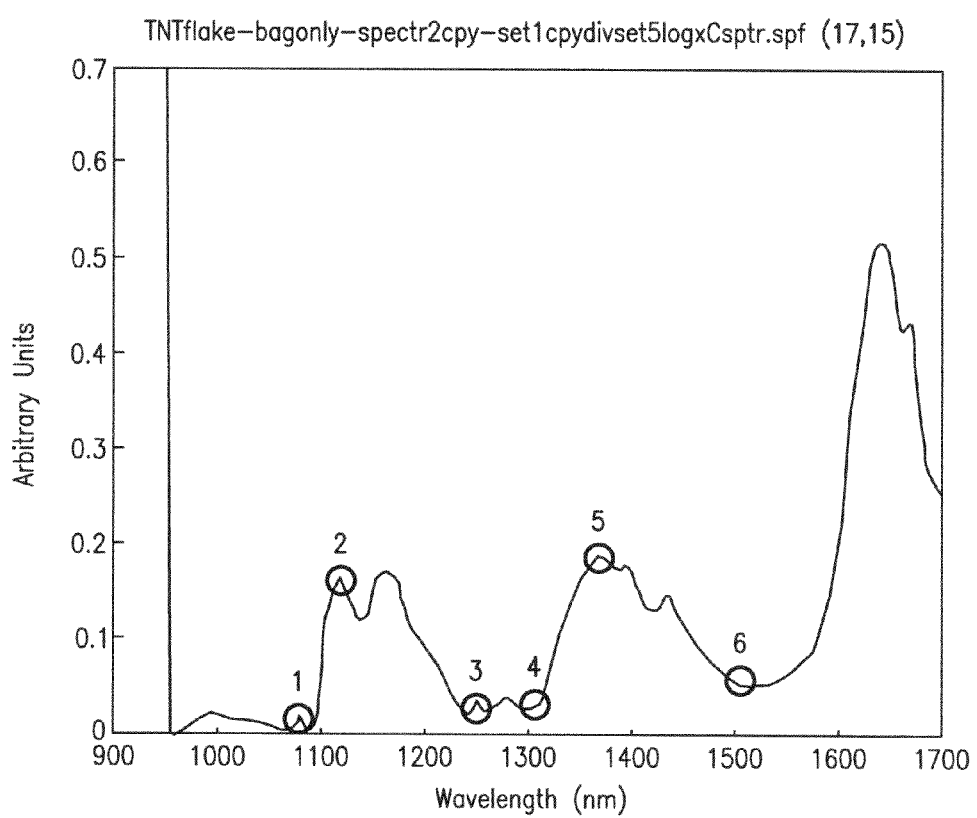
FIG. 7 is a NIR reflection spectra showing the reflectance spectrum of trinitrotoluene (TNT) in flake form contained in a polyethylene antistatic bag held in a polyethylene vest pocket, taken from single pixels of hyperspectral image data, illustrating by the circled points the wavelengths that may be used in generating a 6 wavelength (4 off-peak and 2 peak) differential wavelength image.

In a further preferred embodiment, to even further increase the detection and identification capability of the system and method of the present invention, six sample images at six selected wavelengths or bands of wavelengths are collected. An exemplary resulting NIR spectra is illustrated in FIG. 7. In such a preferred embodiment, the average of two 3 wavelength point differential images obtained by using formula (C) shown above is calculated. Preferably, this process employs a weighting factor in calculating the average of two 3 wavelength point differential images.

In another preferred embodiment, five or more sample images are collected at five or more distinct wavelengths. In this preferred embodiment, one or more multivariate calibration analysis algorithm are applied to each pixel in each differential wavelength image, so as to produce a map of relative concentration of each material of interest. The multivariate calibration analysis algorithms applied in this process are preferably one or more of partial least squares, principal component regression, soft independent modeling of class analogies (SIMCA), k-nearest neighbor (KNN), multi-linear regression, and classical least squares.

Figure 22:
FIG. 22 is a color visible wavelength photograph of a backpack hanging from a wooden board.
Figure 23:
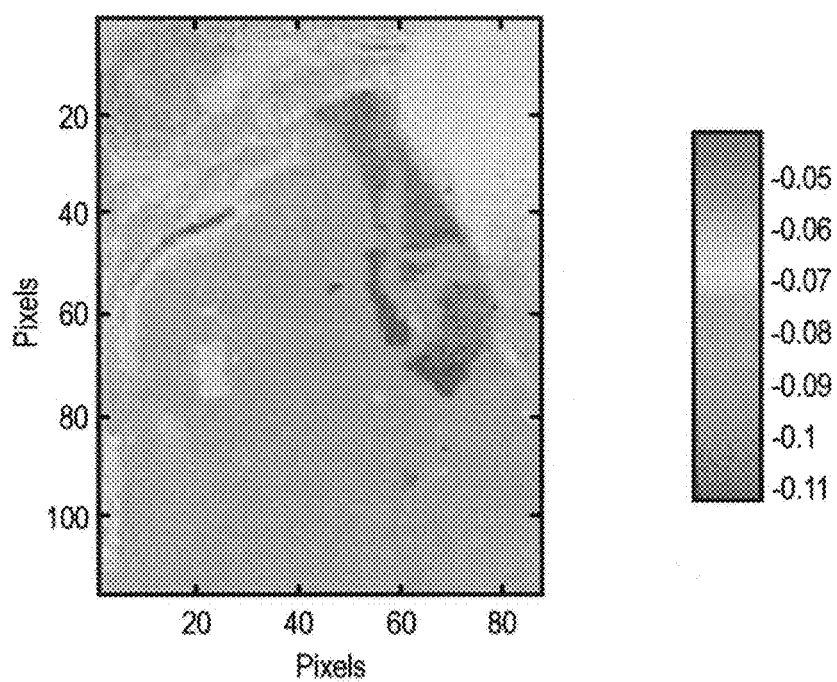
FIG. 23 is a color NIR differential wavelength image taken at 1117-1086 nm of the backpack shown in FIG. 23, the image taken indoors with the system of the present invention, utilizing a 1000 W tungsten halogen lamp at a standoff distance of about 8 ft. from the subject, and a NIR hyperspectral imaging camera at a standoff distance of about 25 ft. from the subject.
Figure 24:
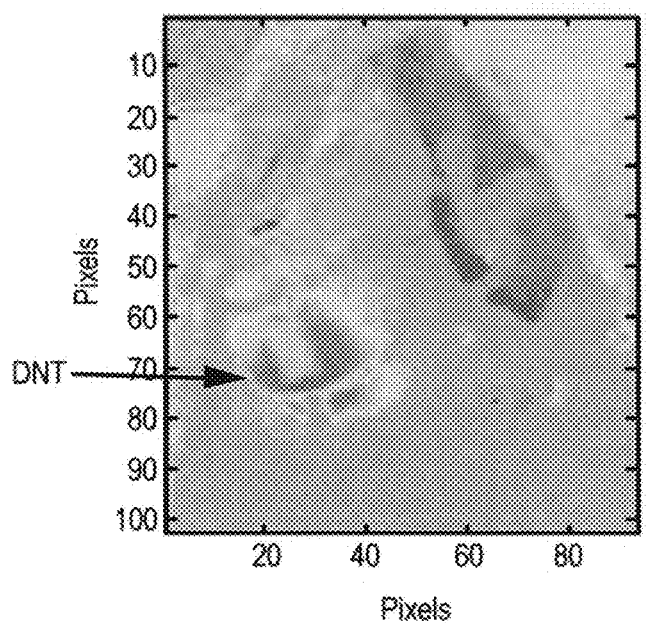
FIG. 24 is a color NIR differential wavelength image taken at 1117-1086 nm of the backpack shown in FIG. 23, further containing a polyethylene bag holding 3 one pound bags of DNT.
Figure 25:
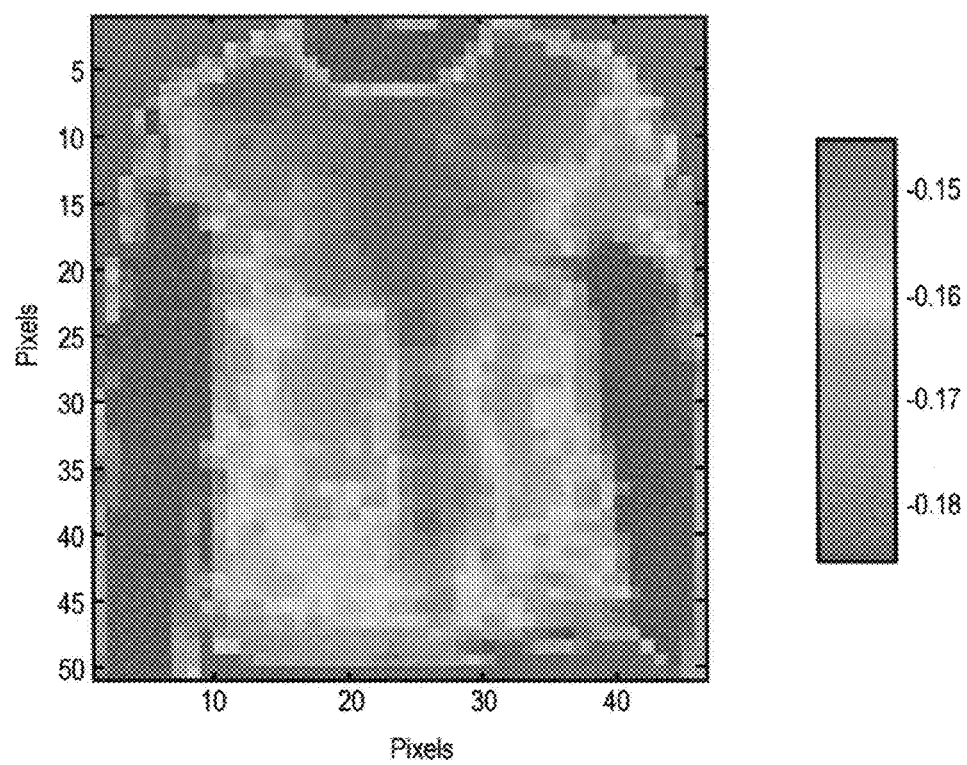
FIG. 25 is a color differential wavelength image with contrast enhancement taken at 1208-1086 nm, with 2 second collections per wavelength, of a male manikin wearing a polyethylene vest having two bags containing 1" cube blocks of TNT, and 3 cloth covering layers thereover, the image taken indoors with the differential wavelength imaging system for detection and identification of concealed materials of the present invention, utilizing four 500 W tungsten halogen lamps at a standoff distance of about 10 ft. from the subject, and a NIR hyperspectral imaging camera at a standoff distance of about 42 ft. from the subject.
Figure 26:
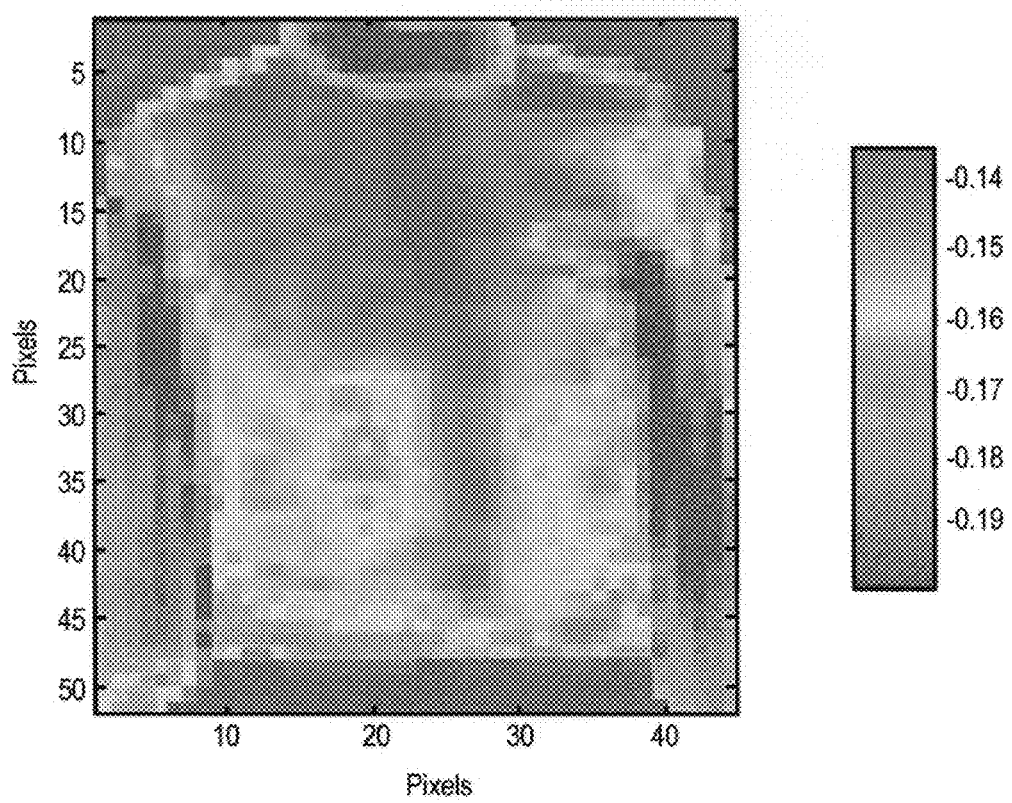
FIG. 26 is a color differential wavelength image with contrast enhancement taken at 1208-1086 nm, with 2 second collections per wavelength, of a male manikin wearing a polyethylene vest having two bags containing 1" cube blocks of PETN, and 3 cloth covering layers thereover, the image taken indoors with the system of the present invention, utilizing four 500 W tungsten halogen lamps at a standoff distance of about 10 ft. from the subject, and a NIR hyperspectral imaging camera at a standoff distance of about 42 ft. from the subject.
Figure 27:
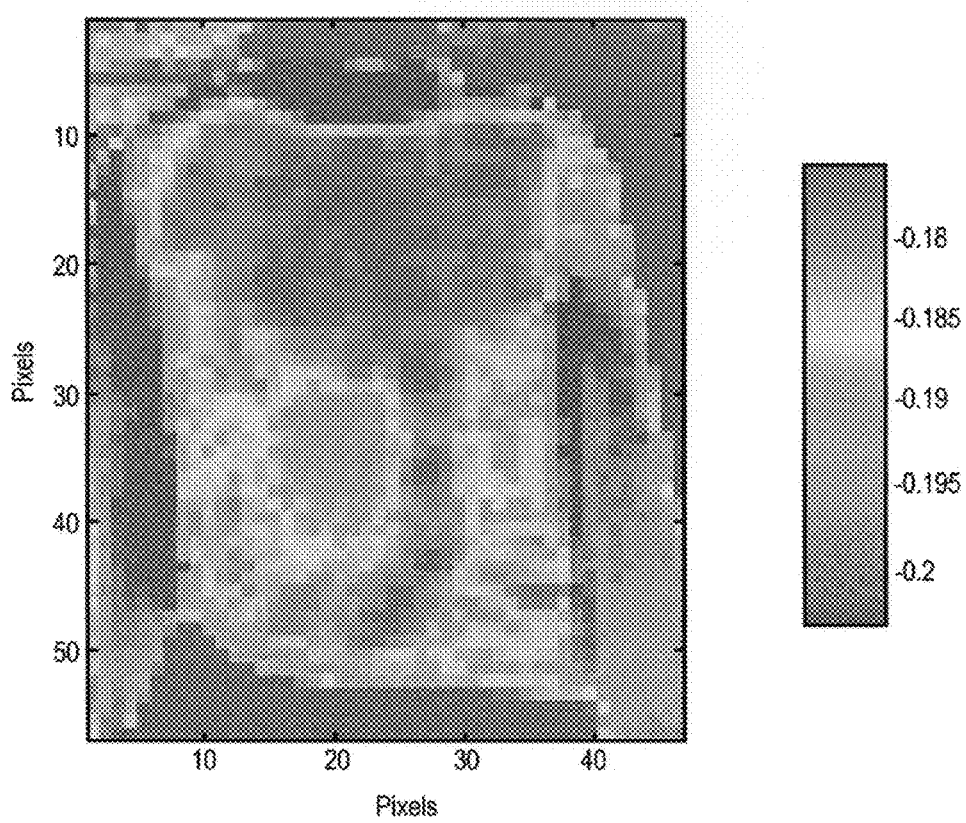
FIG. 27 is a color differential wavelength image with contrast enhancement taken at 1184-1100 nm, with 2 second collections per wavelength, of a male manikin wearing a polyethylene vest having two bags containing RDX, and 3 cloth covering layers thereover, the image taken indoors with the system of the present invention, utilizing four 500 W tungsten halogen lamps at a standoff distance of about 10 ft. from the subject, and a NIR hyperspectral imaging camera at a standoff distance of about 42 ft. from the subject.
Figure 28:
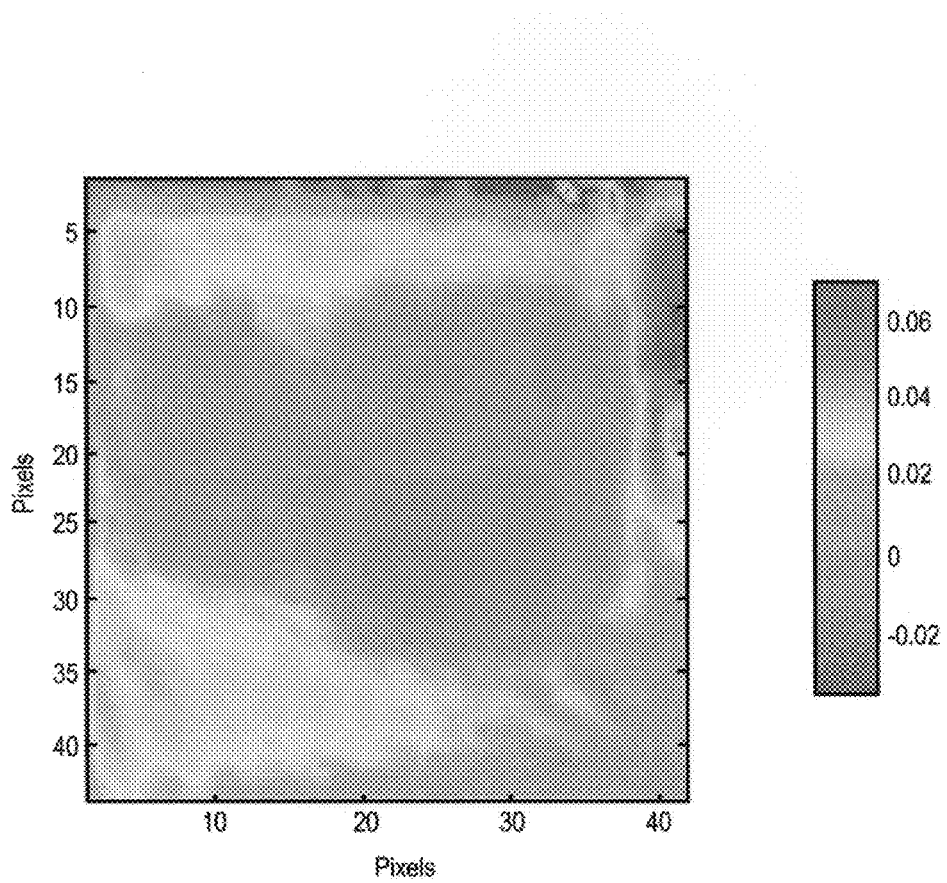
FIG. 28 is a color differential wavelength image using three different wavelength pairs taken at 1388-1250 nm, with 2 second collections per wavelength, of a male manikin having a bag of RDX explosive, a leather wallet and an i-phone cell phone taped to the torso thereof, and one cotton undershirt covering same, the image taken indoors with the system of the present invention, utilizing four 500 W tungsten halogen lamps at a standoff distance of about 10 ft. from the subject, and a NIR hyperspectral imaging camera at a standoff distance of about 25 ft. from the subject.
Figure 29:
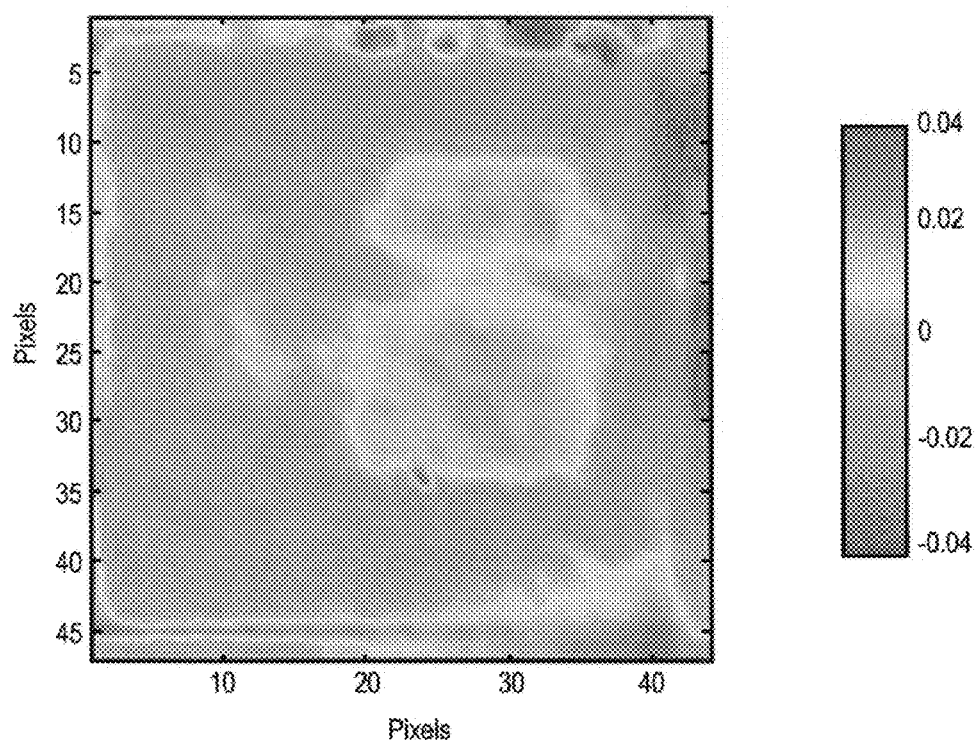
FIG. 29 is a color differential wavelength image using three different wavelength pairs taken at 992-1250 nm, with 2 second collections per wavelength, of a male manikin having a bag of RDX explosive, a leather wallet and an i-phone cell phone taped to the torso thereof, and one cotton undershirt covering same, the image taken indoors with the system of the present invention, utilizing four 500 W tungsten halogen lamps at a standoff distance of about 10 ft. from the subject, and a NIR hyperspectral imaging camera at a standoff distance of about 25 ft. from the subject.

As mentioned above, an object of the present invention is to detect and identify materials concealed under clothing on a human subject, as illustrated in FIGS. 1-2, and 11-21. However, the present method and system are capable of being applied to virtually any covering material. For example, as illustrated in FIGS. 22-24, materials concealed within many different materials, such as the nylon backpack shown in said Figures may be detected and identified.

Further, the present method and system of the present invention have been experimentally determined to be capable of distinguishing many types of everyday objects from known contraband. For example, experimental tests were carried out using a manikin having various objects concealed underneath clothing placed thereon, including TNT explosive, RDX explosive, a leather wallet and an i-phone cell phone taped to the torso thereof. Images were taken of the manikin at various standoff distances, and at various wavelengths. As shown in FIGS. 25-29, regardless of the type and number of clothing layers covering the concealed materials, the concealed materials (including the explosives TNT and DNT) were clearly visible in the color differential wavelength images. Further, the method and system of the present invention quickly and accurately identified the explosive compositions.

Figure 2:
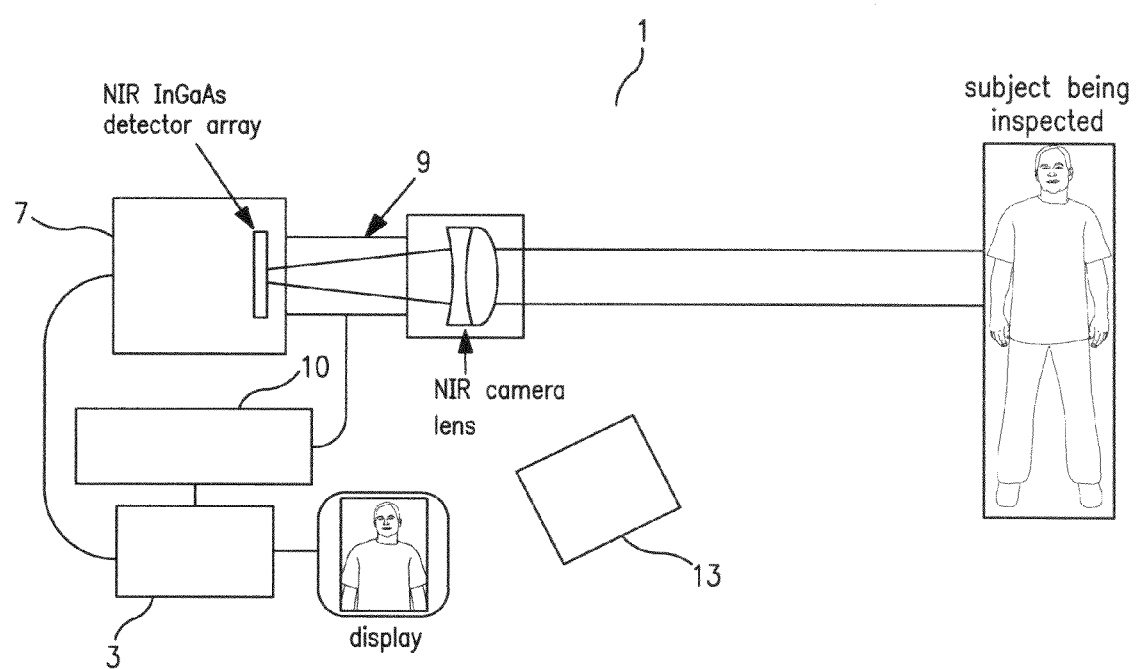
FIG. 2 is a block diagram illustrating the components and connectivity thereof which make up the differential wavelength imaging system for detection and identification of concealed materials, in which a liquid crystal tunable filter is provided.
Figure 3:
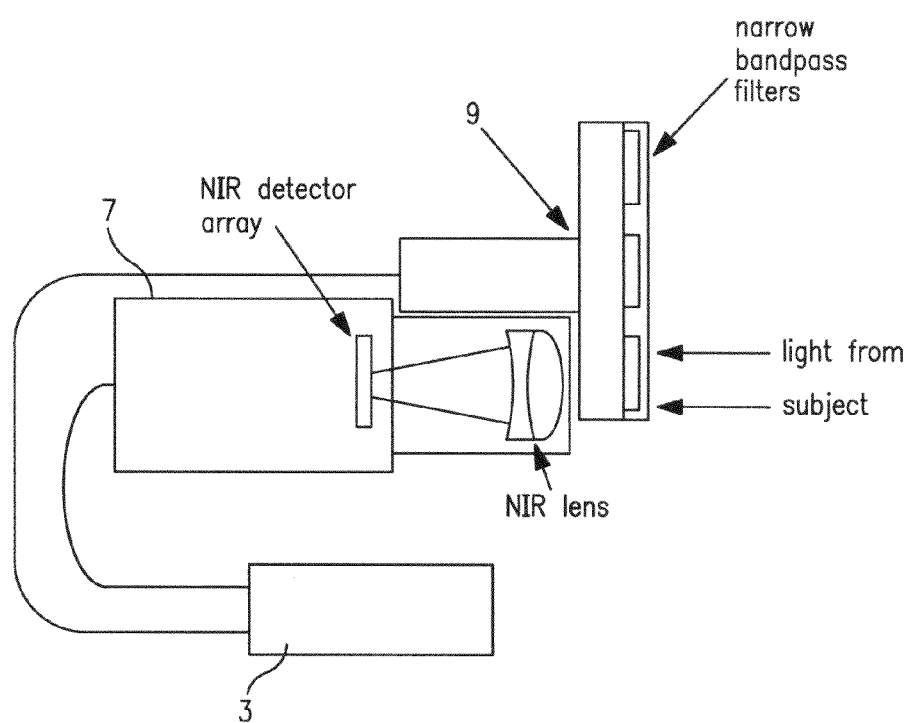
FIG. 3 is a block diagram illustrating the components and connectivity thereof which make up the differential wavelength imaging system for detection and identification of concealed materials, in which a motorized filter wheel is provided.

As a computer-implemented means of carrying out the above-described method, as illustrated in FIGS. 1-3, a system 1 of the present invention is provided, which is generally comprised of a computer 3 and a computer memory storage device 5 in communication with the computer 3. The computer may be a desktop computer, a laptop computer, a PDA, a smart-phone, a game console, a media player or any computing mechanism that performs operations via a microprocessor, which is a programmable digital electronic component that incorporates the functions of a central processing unit (CPU) on a single semi-conducting integrated circuit (IC). One or more microprocessors typically serve as the CPU in a computer system, embedded system, or handheld device.

The system 1 further comprises a NIR signal processing electronics integral with or in communication with the computer, and a near-infrared (NIR) range camera 7 in communication with the NIR signal processing electronics. In a preferred embodiment, the NIR range camera 7 is an InGaAs photodiode array camera or an NIR camera having a continuously variable wavelength narrow bandpass filtering device. The NIR signal processing electronics are not shown, but generally are contained within the camera 7.

In addition, as illustrated in FIGS. 1-3, an optical filtering means 9 is disposed adjacent to or integral with the NIR range camera 7, said optical filtering means 9 operable to filter light at two or more selected wavelengths. The optical filtering means 9 may vary in design, and may be a combination of several filtering means, as long as it is capable of filtering wavelengths into distinct desired regions. For example, in a preferred embodiment, as illustrated in FIG. 2, the optical filter means 9 is an electronically tunable liquid crystal filter including tunable filter control electronics 10. In another preferred embodiment as illustrated in FIG. 3, the filtering means 9 may be a filter wheel comprising a plurality of narrow bandpass filters. Further, filtering devices such as acousto-optic electronically tunable narrow bandpass filters and/or linear continuously graded optical interference filters may be used.

Figure 11:
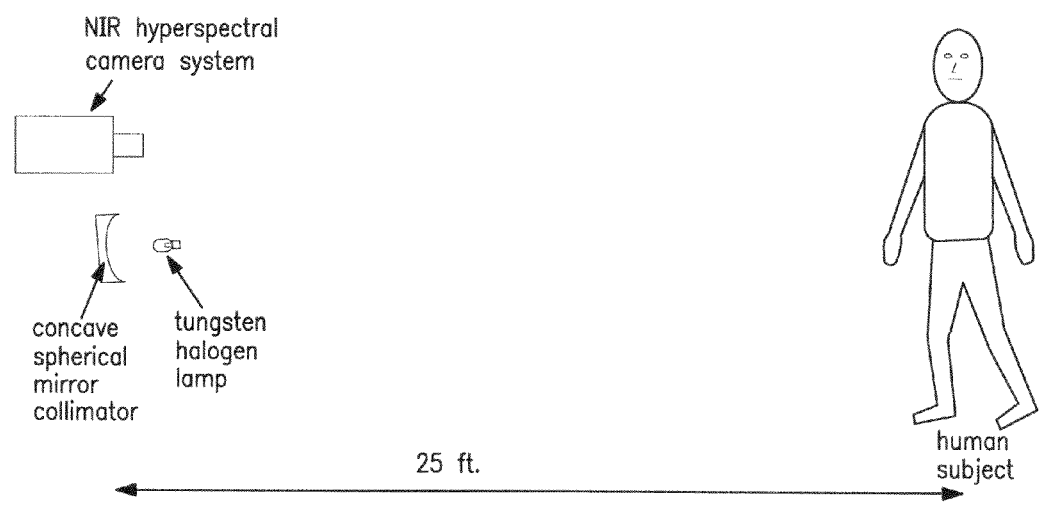
FIG. 11 is a partial side view of an experimental setup of the differential wavelength imaging system for detection and identification of concealed materials of the present invention.
Figure 12:
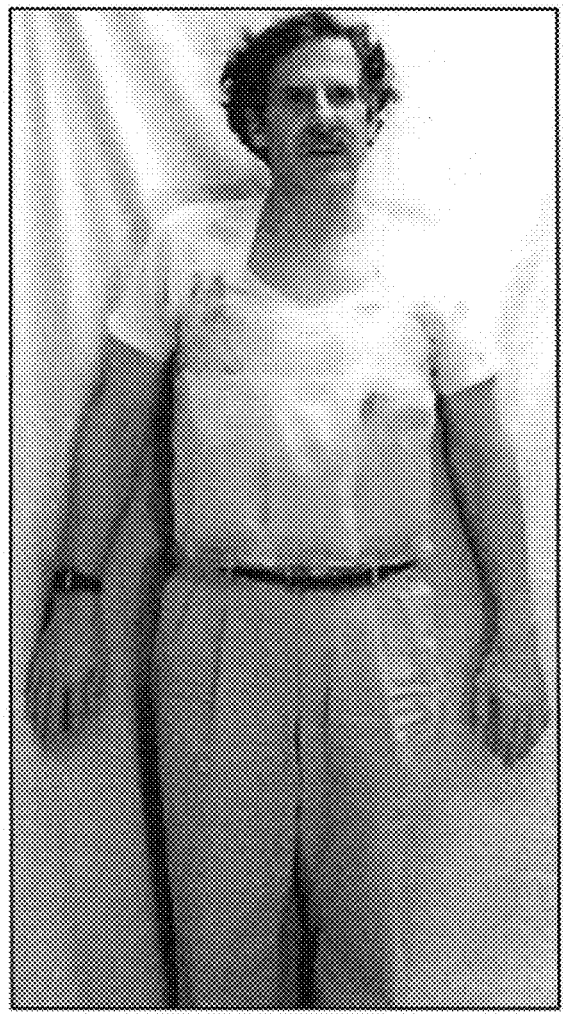
FIG. 12 is a color visible wavelength photograph of a human subject wearing a polyethylene vest containing 3 one pound bags of DNT.
Figure 17:
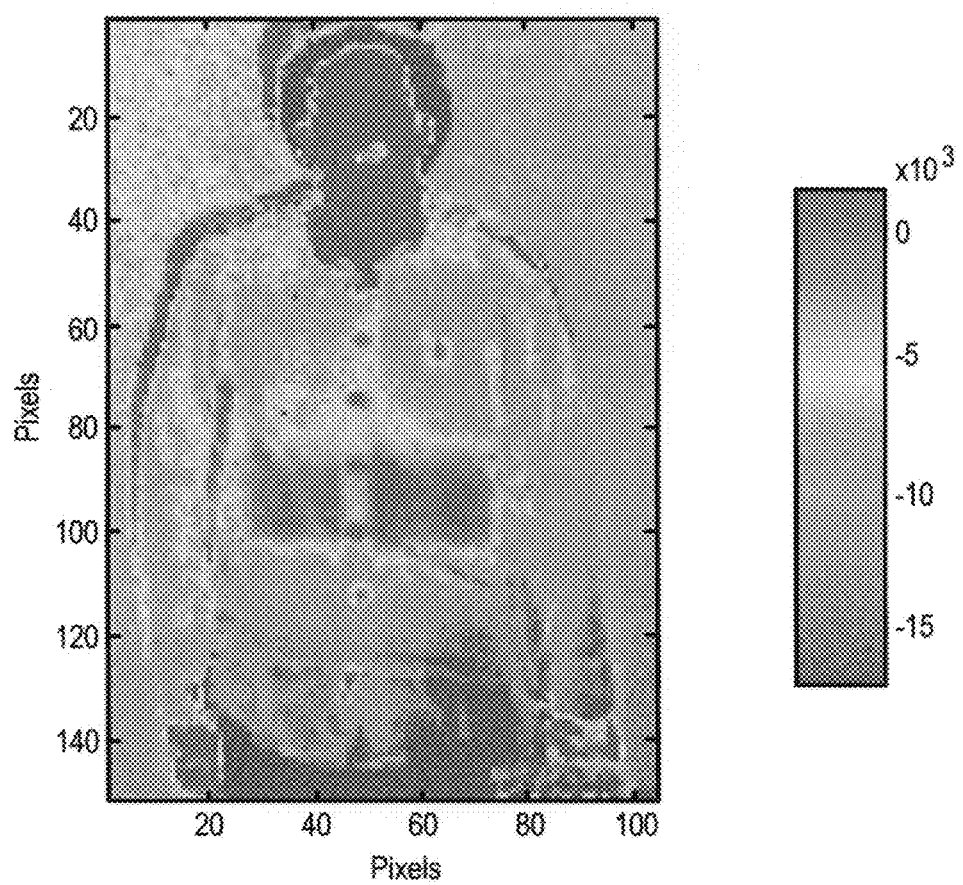
FIG. 17 is a cropped portion of a color NIR differential wavelength image of a human subject wearing a polyethylene vest containing 3 one pound bags of DNT concealed under 3 cloth layers, taken by the system of the present invention utilizing indirect sunlight as the light source, wherein the NIR camera of the present system was placed indoors and the human subject was standing outdoors, with a glass window disposed between the camera and the human subject.

The system of the present invention may further comprise a light source 13 disposed in proximity to the materials of interest, so as to be operable to reflect light thereon. The light source is preferably in communication with the computer 3, so as to be controlled thereby. Any conventional source of light may be used, such as a tungsten halogen lamp as illustrated in FIG. 11. However, the system of the present invention may also function using only ambient/sunlight to illuminate the target of interest, as illustrated in FIGS. 17 and 18.

The present system further comprises a spectral collection and chemical identification application program code embodied on a computer readable medium, for execution on the computer, the application program code being operable to carry out the method of the present invention as described above, i.e., to identify the concealed materials concealed by the covering materials via NIR differential wavelength imaging. Further, the present invention provides a computer executable method of collecting spectral data and identifying one or more chemical substances concealed under covering materials. For the purposes of this description, a computer-usable or computer readable medium can be any apparatus that can contain, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and DVD.

Although specific embodiments of the present invention have been disclosed herein, those having ordinary skill in the art will understand that changes can be made to the specific embodiments without departing from the spirit and scope of the invention. Thus, the scope of the invention is not to be restricted to the specific embodiments. Furthermore, it is intended that the appended claims cover any and all such applications, modifications, and embodiments within the scope of the present invention

LIST OF DRAWING ELEMENTS

1: system for standoff detection and identification of materials of interest concealed by one or more covering materials
3: computer
5: computer memory storage device
7: NIR range camera
9: optical filtering means
10: electronically tunable liquid crystal filter
13: light source

What is claimed is:

1. A differential wavelength imaging method for detection and identification of concealed materials comprising:
   (a) capturing a plurality of sample images of a target at two or more key NIR wavelengths or bands of wavelengths;
   (b) producing a differential wavelength image of the target based on the sample images, the differential wavelength image comprised of a plurality of pixels having a pixel value based on intensity;
   (c) compiling a plurality of differential wavelength image pixel values associated with the sample images to produce total processed image data, and evaluating the total processed image data so as to identify pixels within the differential wavelength image having a higher or lower intensity value than surrounding covering materials; and
   (d) comparing the intensity values of the pixels having a higher or lower intensity value than the covering materials with NIR reflection spectra of known contraband materials to determine correspondence therewith, so as to identify the concealed material(s) associated with the pixels having a higher or lower intensity value than the covering materials.

2. The differential wavelength imaging method for detection and identification of concealed materials of claim 1, further comprising capturing a dark image in step (a), and producing the differential wavelength imaging of the target based on the sample images and the dark image in step (b).

3. The differential wavelength imaging method for detection and identification of concealed materials of claim 1, further comprising producing a user report comprised of an identification of detected concealed materials.

4. A differential wavelength imaging method for detection and identification of concealed materials, said method comprising:
   (i) selecting one or more NIR reflection spectra of known materials collected with no covering material, and one or more NIR spectra of the known materials collected with one or more layers of material covering same;
   (ii) selecting two or more key NIR wavelengths or bands of wavelengths for each NIR reflection spectra of the known materials, said key NIR wavelength or bands of wavelengths corresponding to adjacent peaks and or valleys in the NIR reflection spectra of the known materials;
   (iii) collecting one or more dark images, so as to produce dark image data comprising an image pixel value for each measured pixel;
   (iv) collecting two or more sample images of a sample at each the two or more selected key NIR wavelengths or bands of wavelengths, so as to produce sample image data for each sample image comprising an image pixel value for each measured pixel in each sample image;
   (v) calculating a processed image pixel value for each image pixel, based on the dark image pixel value and each of the sample image pixel values;
   (vi) producing a differential wavelength image by compiling a plurality of the processed image pixel values; and
   (vii) evaluating the differential wavelength image so as to recognize any concealed materials by identifying pixels in the differential wavelength image having a higher or lower intensity value than the known covering materials, and identifying any known concealed materials by comparing each processed image pixel value with the NIR reflection spectra of known materials to determine correspondence therewith.

5. The differential wavelength imaging method for detection and identification of concealed materials of claim 4, wherein evaluating the total processed image data of step (vii) comprises calculating a ratioed intensity value of two or more differential wavelength images, with the images in intensity units, using the following formula A:

$$I_{x,y} = [(lsample^{\lambda 1}_{x,y} - ldark^{\lambda 1}_{x,y})]/[(lsample^{\lambda 2}_{x,y} - ldark^{\lambda 2}x,y)] \quad (A)$$

where $I_{x,y}$ is the processed image pixel value at pixel (x,y), $lsample^{\lambda 1}_{x,y}$ is the sample image pixel value at wavelength $\lambda 1$ and pixel (x,y), $ldark^{\lambda 1}_x$, is the dark image pixel value at wavelength $\lambda 1$ and pixel (x,y), $lsample^{\lambda 2}_{x,y}$ is the sample image pixel value at wavelength $\lambda 2$ and pixel (x,y), and $ldark^{\lambda 2}x,y$ is the dark image pixel value at wavelength $\lambda 2$ and pixel (x,y).

6. The differential wavelength imaging method for detection and identification of concealed materials of claim 4, wherein evaluating the total processed image data of step (vii) comprises determining a processed image pixel value for one or more pixels by calculating a logarithmic value of the ratioed intensity, using the following formula B:

$$\log I_{x,y} = \log [(lsample^{\lambda 1}_{x,y} - ldark^{\lambda 1}_{x,y})/(lsample^{\lambda 2}_{x,y} - ldark^{\lambda 2}x,y)] \quad (B)$$

7. The differential wavelength imaging method for detection and identification of concealed materials of claim 4, wherein when comparing and evaluating the image data corresponding to the key NIR wavelengths, the differential wavelength image is determined with the numerator of the ratio as the wavelength corresponding to an absorption peak of the material of interest, and the denominator corresponding to an absorption valley for ratio processed image data.

8. The differential wavelength imaging method for detection and identification of concealed materials of claim 4, further comprising enhancing the contrast of one or more of the collected image, so as to improve visibility of the concealed materials.

9. The differential wavelength imaging method for detection and identification of concealed materials of claim 8, wherein enhancing contrast of one or more of the collected images is performed by one or more of pixel histogram normalization, linear or non-linear pixel intensity transformation, and transformation of the image into a binary image using a threshold pixel intensity value for separation of 0 and 1 pixels.

10. The differential wavelength imaging method for detection and identification of concealed materials of claim 4, wherein three sample images are collected at three selected wavelengths or bands of wavelengths, and wherein the processed image value for each pixel is calculated using the following formula (C):

$$I_{x,y} = [[[(lsample^{\lambda 1}_{x,y} - ldark^{\lambda 1}_{x,y})]/[(lsample^{\lambda 2}_{x,y} - ldark^{\lambda 2}x,y)]] + [[(lsample^{\lambda 2}_{x,y} - ldark^{\lambda 2}_{x,y})]/[(lsample^{\lambda 3}_{x,y} - ldark^{\lambda 3}x,y)]]]/2 \quad (C)$$

where $I_{x,y}$ is the processed image pixel value at pixel (x,y), $lsample^{\lambda 1}_{x,y}$ is the sample image pixel value at wavelength $\lambda 1$ and pixel (x,y), $ldark^{\lambda 1}_x$, is the dark image pixel value at wavelength $\lambda 1$ and pixel (x,y), $lsample^{\lambda 2}_{x,y}$ is the sample image pixel value at wavelength $\lambda 2$ and pixel (x,y), $ldark^{\lambda 2}x,y$ is the dark image pixel value at wavelength $\lambda 2$ and pixel (x,y), $lsample^{\lambda 3}_{x,y}$ is the sample image pixel value at wavelength $\lambda 3$ and pixel (x,y), and $ldark^{\lambda 3}x,y$ is the dark image pixel value at wavelength $\lambda 3$ and pixel (x,y).

11. The differential wavelength imaging method for detection and identification of concealed materials of claim 10, wherein six sample images are collected at six selected wavelengths or bands of wavelengths, and the average of two 3 wavelength point differential images are calculated using formula (C).

12. The differential wavelength imaging method for detection and identification of concealed materials of claim 11, wherein a weighting factor is employed in calculating the average of two 3 wavelength point differential images.

13. The differential wavelength imaging method for detection and identification of concealed materials of claim 4, wherein five or more sample images are collected at five or more distinct wavelengths, and one or more multivariate calibration analysis algorithms are applied to each pixel in each differential wavelength image, so as to produce a map of relative concentration of each concealed material.

14. The differential wavelength imaging method for detection and identification of concealed materials of claim 13, wherein the multivariate calibration analysis algorithms are one or more selected from the group consisting of partial least squares, principal component regression, soft independent modeling of class analogies (SIMCA), k-nearest neighbor (KNN), multilinear regression, and classical least squares.

15. A system for detection and identification of concealed materials comprising:
   (a) a computer;
   (b) a computer memory storage device in communication with the computer;
   (c) NIR signal processing electronics integral with or in communication with the computer;

(d) a near-infrared (NIR) range camera in communication with the NIR signal processing electronics;

(e) an optical filtering means disposed adjacent to or integral with the NIR range camera, said optical filtering means operable to filter light at two or more selected wavelengths;

(f) spectral collection and chemical identification application program code embodied on a computer readable medium, for execution on the computer, operable to identify the concealed materials concealed by the covering materials via NIR differential wavelength imaging, wherein said chemical identification application program code comprises:

(i) application program code operable to enable selection of one or more NIR reflection spectra of known materials stored on the computer memory storage device, said NIR reflection spectra for each known material comprising an NIR spectra of the known material collected with no covering material, and one or more NIR spectra of the material collected with one or more layers of material covering same;

(ii) application program code operable to select two or more key NIR wavelengths corresponding to adjacent peaks and/or valleys in the NIR spectra for each NIR reflection spectra of the known material;

(iii) application program code operable to enable collection of one or more dark images, so as to produce dark image data comprising an image pixel value for each measured pixel;

(iii) application program code operable to enable collection of two or more sample images of the sample at each of the two or more selected wavelengths or bands of wavelengths, so as to produce sample image data for each sample image comprising an image pixel value for each measured pixel in each sample image;

(iv) application program code operable to calculate a processed image pixel value for each image pixel, based on the dark image pixel value and each of the sample image pixel values;

(v) application program code operable to produce a differential wavelength image by compiling a plurality of processed image pixel values;

(vi) application program code operable to evaluate the total processed image data so as to recognize any concealed materials by identifying pixels having a higher or lower intensity value than the known covering materials, and identify any known concealed materials by comparing each processed image pixel value with the NIR reflection spectra of known materials to determine correspondence therewith;

(vii) application program code operable to produce a user report comprising data concerning one or more of detected known materials, covering materials, and materials of interest.

16. The system for detection and identification of concealed materials of claim 15, further comprising a light source disposed in proximity to the materials of interest, so as to be operable to reflect light thereon.

17. The system for detection and identification of concealed materials of claim 15, wherein the covering materials are comprised of one or more of cotton, cotton/polyester blends, silk, polypropylene, nylon, nylon/cotton blends, rayon, wool, flannel, leather, and combinations thereof.

18. The system for detection and identification of concealed materials of claim 15, wherein the NIR range camera is an InGaAs photodiode array camera or an NIR camera having a continuously variable wavelength narrow bandpass filtering device.

19. The system for detection and identification of concealed materials of claim 15, wherein the optical filtering means is one or more of an electronically tunable liquid crystal filter, an acousto-optic electronically tunable narrow bandpass filter, a linear continuously graded optical interference filter, and a filter wheel comprising a plurality of narrow bandpass filters.

20. The system for detection and identification of concealed materials of claim 15, wherein the application program code operable to evaluate the total processed image data comprised application program code operable to determine a processed image pixel value for one or more pixels by calculating a ratioed intensity value of the two or more differential wavelength images, with the images in intensity units, using the following formula A:

$$I_{x,y} = [(lsample^{\lambda 1}_{x,y} - ldark^{\lambda 1}_{x,y})]/[(lsample^{\lambda 2}_{x,y} - ldark^{\lambda 2}{x,y})] \quad (A)$$

where $I_{x,y}$ is the processed image pixel value at pixel (x,y), $lsample^{\lambda 1}_{x,y}$ is the sample image pixel value at wavelength $\lambda 1$ and pixel (x,y), $ldark^{\lambda 1}_{x,y}$ is the dark image pixel value at wavelength $\lambda 1$ and pixel (x,y), $lsample^{\lambda 2}_{x,y}$ is the sample image pixel value at wavelength $\lambda 2$ and pixel (x,y), and $ldark^{\lambda 2}x,y$ is the dark image pixel value at wavelength $\lambda 2$ and pixel (x,y).

21. The system for detection and identification of concealed materials of claim 15, wherein the application program code operable to evaluate the total processed image data further comprises application program code operable to determine a processed image pixel value for one or more pixels by calculating a logarithmic value of the ratioed intensity, using the following formula B:

$$\log I_{x,y} = \log[(lsample^{\lambda 1}_{x,y} - ldark^{\lambda 1}_{x,y})/(lsample^{\lambda 2}_{x,y} - ldark^{\lambda 2}{x,y})] \quad (B).$$

22. The system for detection and identification of concealed materials of claim 15, wherein, in the application program code operable to compare and evaluate the image data corresponding to the key NIR wavelengths, the differential wavelength image is determined with the numerator of the ratio as the wavelength corresponding to an absorption peak of the material of interest, and the denominator corresponding to an absorption valley for ratio processed image data.

23. The system for detection and identification of concealed materials of claim 15, wherein the spectral collection and chemical identification application program code further comprises:

(viii) application program code operable to enhance the contrast of the collected image, so as to improve visibility of the materials of interest.

24. The system for detection and identification of concealed materials of claim 15, wherein the application program code operable to enhance contrast of the collected image performs one or more functions selected from the group consisting of pixel histogram normalization, linear or non-linear pixel intensity transformation, and transformation of the image into a binary image using a threshold pixel intensity value for separation of 0 and 1 pixels.

25. The system for detection and identification of concealed materials of claim 15, wherein the spectral collection and chemical identification application program code is operable to collect three sample images at three selected key wavelengths or bands of wavelengths, wherein the processed image value for each pixel is calculated using the following formula (C):

$$I_{x,y}=[[[(lsample^{\lambda 1}_{x,y}-ldark^{\lambda 1}_{x,y})]/[(lsample^{\lambda 2}_{x,y}-ldark^{\lambda 2}x,y)]]+[[(lsample^{\lambda 2}_{x,y}-ldark^{\lambda 2}_{x,y})]/[(lsample^{\lambda 3}_{x,y}-ldark^{\lambda 3}x,y)]]]/2 \quad (C)$$

where $I_{x,y}$ is the processed image pixel value at pixel (x,y), $lsample^{\lambda 1}_{x,y}$ is the sample image pixel value at wavelength λ1 and pixel (x,y), $ldark^{\lambda 1}_x$, is the dark image pixel value at wavelength λ1 and pixel (x,y), $lsample^{\lambda 2}_{x,y}$ is the sample image pixel value at wavelength λ2 and pixel (x,y), $ldark^{\lambda 2}x,y$ is the dark image pixel value at wavelength λ2 and pixel (x,y), $lsample^{\lambda 3}_{x,y}$ is the sample image pixel value at wavelength λ3 and pixel (x,y), and $ldark^{\lambda 3}x,y$ is the dark image pixel value at wavelength λ3 and pixel (x,y).

26. The system for detection and identification of concealed materials of claim 15, wherein the spectral collection and chemical identification application program code further is operable to collect six sample images at six selected key wavelengths or bands of wavelengths, further comprising application program code operable to calculate the average of two 3 wavelength point differential images obtained by using formula (C).

27. The system for detection and identification of concealed materials of claim 15, wherein the spectral collection and chemical identification application program code further comprising application program code operable to employ a weighting factor in calculating the average of two 3 wavelength point differential images.

28. The system for detection and identification of concealed materials of claim 15, wherein the spectral collection and chemical identification application program code further is operable to collect five or more sample images at five or more key wavelengths or bands of wavelengths, further comprising application program code operable to apply one or more multivariate calibration analysis algorithm to each pixel in each differential wavelength image, so as to produce a map of relative concentration of each material of interest.

29. The system for detection and identification of concealed materials of claim 15, wherein the multivariate calibration analysis algorithms are one or more selected from the group consisting of partial least squares, principal component regression, soft independent modeling of class analogies (SIMCA), k-nearest neighbor (KNN), multilinear regression, and classical least squares.

* * * * *